US008771170B2

(12) United States Patent
Mesallum et al.

(10) Patent No.: US 8,771,170 B2
(45) Date of Patent: Jul. 8, 2014

(54) METHODS AND APPARATUS FOR TRANSESOPHAGEAL MICROACCESS SURGERY

(75) Inventors: Sameh Mesallum, Quincy, MA (US); James H. Bleck, Chelmsford, MA (US)

(73) Assignee: Microaccess, Inc., Quincy, MA (US)

( * ) Notice: Subject to any disclaimer, the term of this patent is extended or adjusted under 35 U.S.C. 154(b) by 593 days.

(21) Appl. No.: 12/462,268

(22) Filed: Jul. 31, 2009

(65) Prior Publication Data

US 2010/0036197 A1 Feb. 11, 2010

Related U.S. Application Data

(60) Provisional application No. 61/137,690, filed on Aug. 1, 2008.

(51) Int. Cl.
*A61B 1/00* (2006.01)

(52) U.S. Cl.
USPC .......................................................... 600/104

(58) Field of Classification Search
USPC ..................... 600/201–204, 104; 604/164.01, 604/167.01–167.04; 128/850
See application file for complete search history.

(56) References Cited

U.S. PATENT DOCUMENTS

| | | | |
|---|---|---|---|
| 3,853,117 A | | 12/1974 | Murr |
| 3,960,143 A | * | 6/1976 | Terada .......................... 600/104 |
| 4,233,984 A | | 11/1980 | Walling |
| 4,501,264 A | * | 2/1985 | Rockey ......................... 128/898 |
| 4,671,295 A | | 6/1987 | Abrams et al. |

(Continued)

FOREIGN PATENT DOCUMENTS

| | | |
|---|---|---|
| WO | 02/38201 A2 | 5/2002 |
| WO | 2005072445 A2 | 8/2005 |

(Continued)

OTHER PUBLICATIONS

BMJ—Microaccess published article vol. 20 No. 3 Sep. 2003; Benha M.J.

(Continued)

*Primary Examiner* — Matthew Lawson
*Assistant Examiner* — Zade Coley
(74) *Attorney, Agent, or Firm* — Lando & Anastasi, LLC

(57) ABSTRACT

The current invention describes methods of transesophageal access to the neck and thorax to perform surgical interventions on structures outside the esophagus in both the cervical and the thoracic cavity. It describes a liner device made of a complete or partial tubular structure, or a flat plate, the liner having means to facilitate creation of a side opening, which may include a valve. The liner with its side opening form a port structure inside the esophageal lumen. The port structure allows elongated surgical devices to pass through a perforation across the full thickness of the esophageal wall to outside location, in a controlled way. The elongated surgical devices can be diagnostic scopes, therapeutic scopes, manual elongated surgical devices, robotic arms or the like. After being deployed outside the esophagus, the surgical devices can access structures outside the esophagus, in the neck and thorax in 360 degrees of freedom around the esophageal circumference. These structures can be bony, cartilaginous, spinal, vascular, soft tissue, deep tissues, lymph nodal, cardiac, pulmonary, tracheal, nervous, muscular or diaphragmatic, skin and subcutaneous tissues of the neck, skin and subcutaneous tissues of the anterior chest wall, skin and subcutaneous tissues of the skin of the back, and skin and layers of the breast.

10 Claims, 15 Drawing Sheets

(56) References Cited

U.S. PATENT DOCUMENTS

| | | | |
|---|---|---|---|
| 4,763,653 A * | 8/1988 | Rockey | 606/194 |
| 4,886,059 A * | 12/1989 | Weber | 128/207.15 |
| 5,247,938 A | 9/1993 | Silverstein et al. | |
| 5,297,536 A * | 3/1994 | Wilk | 600/104 |
| 5,309,896 A * | 5/1994 | Moll et al. | 600/207 |
| 5,314,473 A * | 5/1994 | Godin | 623/23.68 |
| 5,315,992 A | 5/1994 | Dalton | |
| 5,366,490 A * | 11/1994 | Edwards et al. | 607/99 |
| 5,382,231 A * | 1/1995 | Shlain | 128/898 |
| 5,406,950 A | 4/1995 | Brandenburger et al. | |
| 5,458,131 A * | 10/1995 | Wilk | 600/105 |
| 5,467,100 A | 11/1995 | Chen | |
| 5,476,100 A | 12/1995 | Galel | |
| 5,562,603 A * | 10/1996 | Moll et al. | 600/204 |
| 5,599,294 A * | 2/1997 | Edwards et al. | 604/22 |
| 5,611,344 A | 3/1997 | Bernstein et al. | |
| 5,704,361 A | 1/1998 | Seward et al. | |
| 5,735,831 A * | 4/1998 | Johnson et al. | 604/523 |
| 5,752,938 A * | 5/1998 | Flatland et al. | 604/167.01 |
| 5,775,328 A | 7/1998 | Lowe et al. | |
| 5,810,757 A | 9/1998 | Sweezer, Jr. et al. | |
| 5,837,221 A | 11/1998 | Bernstein et al. | |
| 5,853,698 A | 12/1998 | Straub et al. | |
| 5,855,614 A | 1/1999 | Stevens et al. | |
| 5,910,111 A * | 6/1999 | Hunziker | 600/407 |
| 5,924,424 A | 7/1999 | Stevens et al. | |
| 5,944,019 A | 8/1999 | Knudson et al. | |
| 5,957,849 A | 9/1999 | Munro | |
| 6,026,814 A | 2/2000 | LaFontaine et al. | |
| 6,030,365 A | 2/2000 | Laufer | |
| 6,193,680 B1 * | 2/2001 | Parsons et al. | 601/149 |
| 6,258,087 B1 * | 7/2001 | Edwards et al. | 606/41 |
| 6,296,654 B1 | 10/2001 | Ward | |
| 6,423,058 B1 * | 7/2002 | Edwards et al. | 606/41 |
| 6,689,062 B1 | 2/2004 | Mesallum | |
| 6,740,101 B2 * | 5/2004 | Houser et al. | 606/153 |
| 6,908,427 B2 | 6/2005 | Fleener et al. | 600/104 |
| 7,048,014 B2 * | 5/2006 | Hyodoh et al. | 140/92.1 |
| 7,507,238 B2 * | 3/2009 | Edwards et al. | 606/41 |
| 8,070,680 B2 | 12/2011 | Mesallum | |
| 2001/0049497 A1 | 12/2001 | Kalloo et al. | |
| 2004/0097801 A1 | 5/2004 | Mesallum | |
| 2005/0075622 A1 * | 4/2005 | Levine et al. | 604/500 |
| 2005/0222678 A1 * | 10/2005 | Lashinski et al. | 623/2.11 |
| 2006/0259030 A1 * | 11/2006 | Utley et al. | 606/41 |
| 2007/0239022 A1 * | 10/2007 | Harhen | 600/459 |
| 2010/0217367 A1 | 8/2010 | Belson | |
| 2013/0066304 A1 | 3/2013 | Belson et al. | |
| 2013/0150832 A1 | 6/2013 | Belson et al. | |
| 2013/0150871 A1 | 6/2013 | Belson et al. | |
| 2013/0211196 A1 | 8/2013 | Belson et al. | |

FOREIGN PATENT DOCUMENTS

| | | |
|---|---|---|
| WO | 2007149588 A2 | 12/2007 |
| WO | 2009097461 A1 | 8/2009 |
| WO | 2010/098871 A2 | 9/2010 |

OTHER PUBLICATIONS

"A prospective randomized trial of esop"; BG Turner, MC Kim, DW Gee, A. Dursun, M. Mino-Kenudson, ES Huang, P. Sylla, DW Rattner, WR Brugge; Apr. 2011; 785-90.

"Endoscopid transesophageal mediastina"; BG Turner, DW Gee, S. Cizginer, MC Kim, M. Mino-Kenudson, P. Sylla, WR Brugge, DW Rattner; Oct. 2010; 831-5.

"Transesophageal mediastinoscopy by submucosal endoscopy with mucosal flap safety valve technique"; K. Sumiyama, CJ Gostout, E. Rajan, TA Bakken, MA Knipschield; Apr. 2007, 679-83.

"Natural orifice transesophageal mediasatinoscopy and thoracoscopy", FF Willingham, DW Gee, GY Lauwers, WR Brugge, DW Rattner; Apr. 2008; 1042-7.

"Natural orifice transluminal endoscopic surgery"; A. Fritscher-Ravens, K. Patek, A. Ghanbari, E. Kahle, A von Herbay, T. Fritscher, H. Niemann, P. Koehler; Oct. 2007; 870-5.

"Stent placement provides safe esophagea closure in thoracic procedures"; BG Turner, S. Cizginer, MC Kim, M. Mino-Kenudson, RW Ducharme, VC Surti, P. Sylla, WR Brugge, Mar. 2011, 913-8.

* cited by examiner

FIGURE 5
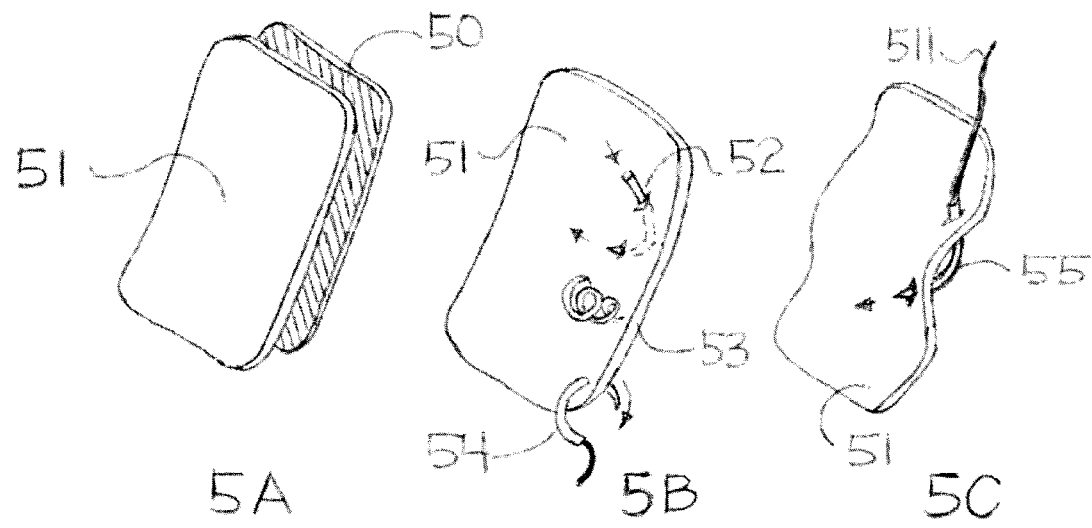
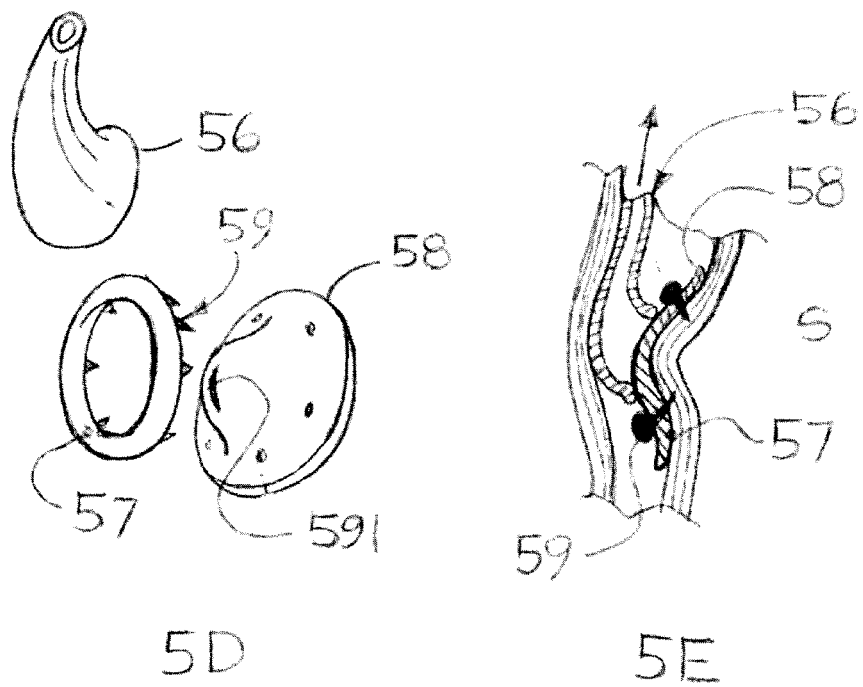

FIGURE 7
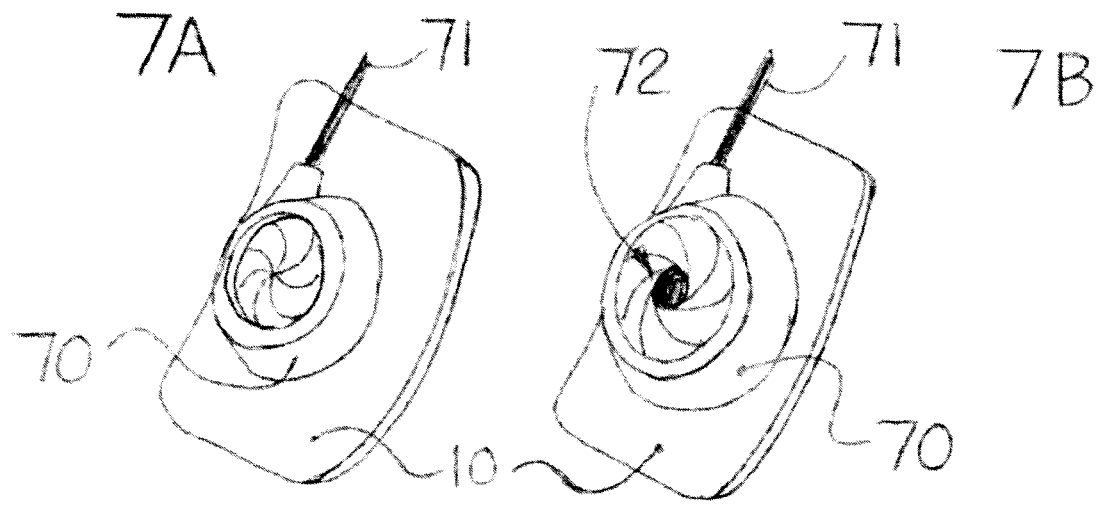
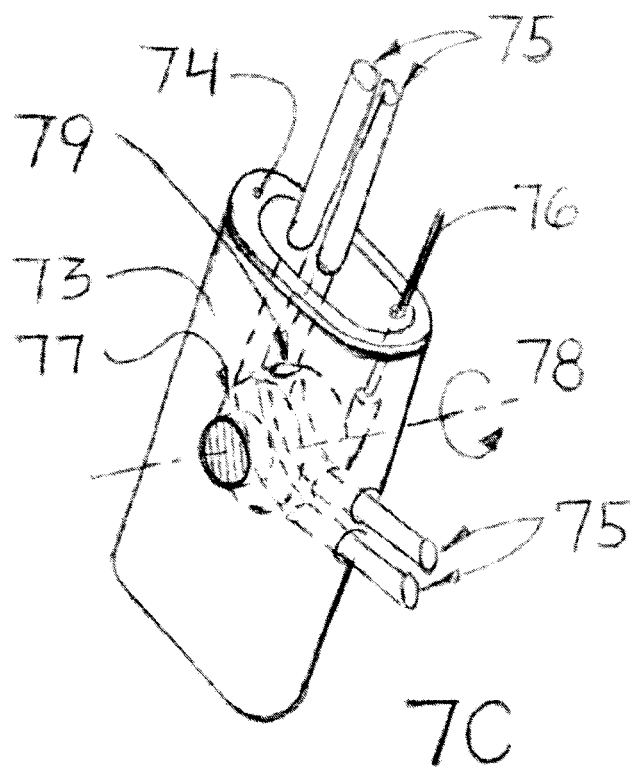

METHODS AND APPARATUS FOR TRANSESOPHAGEAL MICROACCESS SURGERY

CROSS-REFERENCE TO RELATED APPLICATIONS

This application claims the benefit of the priority of US provisional application No. 61/137,690, filed on Aug. 1, 2008, which is incorporated herein by reference in its entirety.

FIELD OF THE INVENTION

The present invention relates generally to a minimally invasive approach to perform transesophageal surgical, orthopedic and neurosurgical procedures in the mediastinum, cervical and thoracic cavities. The invention describes devices and methods to create a transesophageal access to said structures and surrounding structures to perform a body of surgical procedures while the heart is beating with or without the need for general anesthesia. A key improvement in access to these spaces is provided by provision of an intra-esophageal liner to facilitate transesophageal passage and to reinforce such passages; and to provide, or to catty means for providing, for the sealing of openings through the esophageal wall to prevent permeation of fluids into adjacent compartments, unless desired. These technical improvements are applicable to all forms of transesophageal surgery, and perhaps to other types of surgery as well.

BACKGROUND OF THE INVENTION

Access to the human heart, the thoracic cavity, the neck structures, the cervical spine and the dorsal spine has always been difficult and a source of active research, especially recently with the advancement in technology that has led to improved methods of minimally invasive surgery, orthopedic procedures and neurosurgical procedures. Heart disease is the leading cause of death connected to all age groups in the United States. The esophagus has a close proximity to the heart and the posterior mediastinum, which has allowed the use of transesophageal fine needle aspiration and transesophageal biopsy techniques to be used extensively in recent years to obtain tissue samples. Most of the posterior mediastinal tissues are accessible for biopsy by this route, including the lungs and lymph nodes. The technique has proven to be safe and reproducible with minimal complications. A discussion of such techniques and some of their key uses can be found in U.S. Pat. No. 6,689,062 and in related pending cases, which provide a full background describing this promising new technique. Other groups are also exploring transesophageal surgery, as described for example in WO 2007/149588. In exploring this new area of minimally invasive surgery, it has been found that one of the important but difficult details that need improvement is managing the passage of instruments across the esophageal wall. Surgery via the esophagus has numerous attractions for thoracic and cervical surgeries, but precision location of the entry site, and reliable and simple closure of the site after surgery each present novel problems and require new approaches. We present herein an improved technology for such control.

SUMMARY OF THE INVENTION

Accordingly, it is a principal object of the invention to provide novel methods and means for locating, using, and closing sites in the esophagus for performing transesophageal surgery at any of the previously described sites, or others that may become useful.

In one aspect, a liner (also called a "liner device" herein) is used to demarcate the selected areas of the esophagus. The liner is a piece of a material which is placed at the selected site, optionally with the assistance of imaging techniques. The liner is made of a biocompatible material and optionally is degradable in situ. The liner may be affixed to the selected site via any of several methods. These include adhesives, vacuum, mechanical affixing devices, and simple passive positioning. The liner has numerous optional additional properties, including transparency for visibility; prefabricated penetration locations; radioopaque markers or other location aids; and carriage of other devices, including device sensing and control means, taking advantage of the propinquity of the esophagus to the heart and other organs that might be monitored following a procedure.

The invention provides procedures that can safely and accurately create a transesophageal access into the mediastinum, the thoracic cavity and the cervical cavity. The procedures can be carried out without the need for stopping the heart, or for cardiopulmonary bypass, general anesthesia, or gross or minor thoracotomy. This transesophageal access as described herein can be used to perform a variety of diagnostic and therapeutic surgical, orthopedic and neurosurgical procedures.

The invention comprises a liner device for facilitating the controlled and reversible creation of an opening in the wall of a body lumen, for example the esophagus, through which an endoscopic device can be inserted to perform surgery in adjacent tissues, particularly in the cervical and thoracic regions. The liner device is a structure that lines part of the lumen walls of a hollow body organ or body cavity, in proximity to an organ or a structure outside the lumen structure. The invention deals in particular with the lumen of the esophagus, as a lumen of particular value for the use of the invention. However, any body lumen or cavity can be used for the same techniques, sometimes with certain modifications in each specific case. The lumen liner device allows for elongated surgical devices to be deployed across the lumen wall, to target extraluminal organs or structures for the performance of diagnostic and therapeutic procedures.

The liner device may have a side opening mechanism with or without a supporting structure. The liner device may be of any convenient form, including without limitation a complete tubular structure, an incomplete or partial tubular structure, a curtain-like covering, or a generally planar structure, including for example a plate or patch. The complete tubular liner has two ends, with a side opening, or a location at with a side opening can be created, somewhere on the sidewall between the two ends. The incomplete tubular liner is any cutoff section of a cylinder with a side opening on its wall. The rest of the cutoff section is used for fixation. The plate or patch is any flat structure large enough to cover the perforation in the wall. The plate or patch may also comprise or consist essentially of mechanisms for opening and closing an opening in the lumenal wall ("side opening mechanisms", or SOM).

In general, the liner is held in place by adhesive means and/or mechanical means, and optionally is temporarily held in place by an inflatable balloon or other temporary mechanism. The liner is eventually removed, or is manufactured so as to detach or degrade in situ. The side opening in the liner is a partial or complete passage through the liner to give access to the adjacent or nearby tissue of the lumen, such as the esophagus. In use, an endoscopic instrument is directed to the opening in the liner, and passes through the opening, with completion of the opening in the liner if required, followed by passage through a nearby portion of the esophagus or other lumenal tissue.

After removal of the instrument, the opening created in the lumen is at least partially closed by passive or active blocking of the opening. In one embodiment, the liner is flexible but tends to return to its original shape, which typically is a shape which fits the wall of the body lumen. Then, after passage of an endoscope through the liner and the wall of the lumen, and its removal after surgery, the opening tends to be closed by the relaxation of the liner.

In other embodiments, the opening in the liner is actively closed by the surgeon or other operator, in addition to or in replacement of passive closing. In one embodiment, the side opening is a mechanism that can be deployed mechanically or electronically (wired or wireless), for example by means of the action of an endoscope inside the liner.

In some embodiments there are two liners, nested inside each other and sliding with respect to each other along or around the inside of the lumen. In one embodiment each tube has a side opening. In one position, both side openings are aligned together in one open position. Any rotation or longitudinal motion of either tube closes the opening by de-aligning the side openings away from each other. In other embodiments, the liner side-opening is a camera-like shutter mechanism; or, the liner may have a side opening as a flap of the side wall.

In some embodiments, the liner is fixed to the esophageal wall. There are multiple methods of fixation of the liner circumferentially to the esophageal wall. The particular details of fixation of the liner to the lumenal wall are not critical aspects of the invention, and can include, without limitation, liner fixed to the esophageal wall by means of hooks or spikes, or by glue. The liner can be fixed in position by other means such as vacuum, stitching, stapling, suturing, welding or balloon inflation.

The upper and lower ends of the liner can be closed by diaphragms to prevent any fluid or contamination from entering into the surgical field from above or below. At least the upper diaphragm will typically have a slit or other means to allow for passage of an endoscope. The liner can also have balloons on the proximal and/or distal ends to prevent fluid contamination from above or below.

The liner can also carry other devices, including for example a CCD chip or other chips that can convey images of the liner position in the esophagus, of the liner lumen or of images through the side opening. The liner can also be equipped with operative elements such as piezoelectric cells for ultrasound guidance either alone or combined with transesophageal ultrasound for stereoscopic recognition. The liner can also be powered for motor or mechanical movement, heart treatment, cryotherapy, or magnetic or electromagnetic wave production/reception. All such enhancements are optional, and may instead be provide by other means in lumens that use liners for the basic purpose of controlling instrument penetration and flow through the tissue of the wall of a lumen, particularly the esophageal lumen.

The liner can be made of two layers sliding on each other, for example for longitudinal movement upwards or downwards. This general design also can be used for alignment design of two-sided openings, with a variety of directions in which overlap of holes on opposite sides of the device can be created to allow passage to instruments, or abolished or prevented to deny passage to fluids and the like. These mechanisms are distinct from a non-moving SOM (side opening mechanism), in which generally a mechanical element, for example a shutter is moveable by an endoscope instrument or other means to open and close openings through the lumen of an organ, such as the esophagus. In general, closeable opposed holes will be used for simple cases, and more complex closure devices will be used when multiple or repeated access is likely to be needed.

In other aspects of the invention, the liner is made to fit to the outside surface of an endoscope so that it can be delivered to a target location. The portion of the scope carrying the liner can have one or more means for visualization of the lumen wall to assist in accurate placement. The liner may be fixed, inflated and attached to the esophageal wall in the target segment. When the liner is placed, it is oriented so that the side opening mechanism (SOM) is facing the target area or organ outside the esophagus.

In one example, the side opening mechanism is facing posteriorly towards the thoracic spine. A scope is passed through the SOM to the thoracic spine for a variety of procedures that can be performed from this location, including interventions on the vertebral column, disks, nerves and related structures, disk removal, disk excision or lysis, laser application or cuts, bony or cartilaginous interventions, biopsies, tumor removal, bone removal, spinal cord manipulations, nerve root treatment or injection, and the like.

In another example, the side opening mechanism is facing anteriorly to the heart, and is used for a variety of procedures including atrial mapping and ablation, treatment of arrhythmia, valvular heart disease treatments, occlusion of septal defects, etc. The side-opening mechanism may be facing anteriorly towards the lungs and anterior mediastinum for a variety of procedures both diagnostic or therapeutic, directly or in related structures, with the procedures including biopsy, tumor staging, imaging, injection, delivery of materials, cryotherapy, RF treatment, and laser treatment on tissues including lungs, great vessels, trachea, LN, esophagus, nerves, diaphragm, and lymphatics.

The invention comprises means for improved surgical procedures, and methods for their use. In one aspect, means are provided for isolating esophageal lumen tissue from contact with fluids, said means comprising a liner which is applied to said tissue to cover said tissue on at least one of the inside and the outside of said lumen. In another aspect, said liner has a preformed location for creation of a hole to allow for passage through said liner, and may have a valve mechanism is placed in contact with said hole, and/or a closed distal end. Said valve mechanism can be operated during a procedure affecting at least one of said esophageal tissue, and other tissue accessible through said hole. Said liner may further comprise a side opening mechanism.

The liner device may be affixed to tissue by at least one attachment means, which may comprise at least one of vacuum, mechanical force, balloon inflation, welding, suturing, adhesives including glues, and mechanical devices including hooks, pins, frames, rings and rods. The material of said liner may be characterized in being one or more of degradable in vivo, antimicrobial in effect, and having more than one layer.

The liner device may be deployed with the use of a deployment device, in which said deployment device is sufficiently long that it may be passed through a patient's mouth and advanced to at least the distal esophagus, and still have its proximal end outside of the patient's body. The liner typically has a form selected from a shield, a cut section of a tubular structure or an incomplete tubular structure, or a complete tubular or cylindrical structure.

The invention also comprises a method of performing transesophageal surgery by placing a liner in a target segment in the esophagus, wherein the liner is a barrier and may comprise a complete or partial side opening to allow devices to go through the esophageal wall to a target structure/organ outside the esophageal wall after the liner and the esophageal wall have been penetrated to create an opening. Said side opening can be closed by one or more of spontaneous closure upon withdrawal of an instrument; active closure of a valve; and the activation of a side opening mechanism (SOM).

In this method, the opening may placed in either or both of the cervical and thoracic regions of the esophagus, and it typically faces at least one of posteriorly, laterally, and anteriorly. The liner may be used in procedures including but not limited to tumor excision or biopsy; placement of drugs, tissues, and radioactive materials; bronchial biopsy, airway bypass, manipulation of great vessels of the thorax, and pulmonary artery bypass. The procedures to be performed may include disk surgery, vertebral column surgery, spinal cord surgery, nerve root surgery, spinal and paraspinal muscle surgery, vascular surgery, oncologic surgery, laser surgery, delivery of energy to tissue, delivery of tissue or genetic material, delivery of surgical devices in general, delivery of cardiac pacemaker or diaphragmatic pace maker, and performance of procedures affecting the esophagus itself including fundoplication, and stomach pacemaker implantation. The procedures to be performed may include cardiac procedures including mapping, cardiac ablation, valve surgery, closure of septal defects, laser surgery, delivery of energy to the heart and related structure for pacing or to enhance contractility, delivery of drugs or genetic material, and delivery of surgical devices to the heart and related structures.

The procedures to be performed include procedures on the lungs, bronchi, nerves, lymphatics, great vessels of the thorax, bony or cartilaginous structures, diaphragm, phrenic nerve, gastroesophageal junction and on the esophagus itself, including the delivery of an esophageal band for satiety or an intra-esophageal valve for reflux.

The invention further comprises a method wherein more than one side opening may be created in the esophagus, by one or both of use of at least one liner having more than one side opening, and use of more than one liners having at least one side opening. In addition, a liner may be placed in a tubular body lumen, including the esophagus, the intestine, the genitourinary (GU) tract, the cardiovascular system, the pulmonary system, the canaliculi of the inner ear, and the lymphatic system.

In addition, the liner, or the opening in said tubular body lumen wall, can be sprayed or painted with sealant material to enhance closure of the perforation site. Any sealant can be used, including foam, glue, collagen, and the like.

Any endoscope may be used in the invention, including but not limited to one or more of a conventional scope, a therapeutic scope with custom made specifications, a robotic scope or a remotely operated scope, such as a telemedical or telesurgical scope.

A liner device of the invention may serve to isolate a partial or full perforation in the wall of the esophagus, wherein the isolation of the perforated portion of said wall prevents contamination of the perforation site by covering it. Said liner device may be one of a generally planar device and a device that is fully or partially tubular.

BRIEF DESCRIPTION OF THE FIGURES

FIG. 5 shows liner devices being deployed with the aid of fastening systems.
FIG. 7 shows the use of valves to regulate fluid passage through a liner.

DETAILED DESCRIPTION OF THE INVENTION

A novel liner device is described herein that is used for the isolation of a partial or full thickness perforation in the wall of a luminal body structure or a body cavity. The liner device is passed through the esophagus to a site on the wall of the esophagus, where it is used to isolate a perforation of the esophagus from contact with body fluids. The liner may be applied on the inside, the outside, or both sides of the esophageal lumen. The isolation of a perforated portion of the esophageal lumenal wall allows the perforation to heal while the liner device prevents direct communication or contact between the perforation site and the lumen of said organ or cavity. Because of the normally rapid healing of the esophagus, an isolation period of 24 hours or more is often sufficient.

The liner or ancillary devices may also isolate structures surrounding the lumen, by blocking flow from the inside of the lumen, or by directly treating structures outside of the lumen, including the outside of the lumen. The liner prevents contamination of a perforation site by covering the site, and can keep the perforation edges free of contamination until healing occurs spontaneously, or until mechanical approximation of the edges of the perforation.

The liner device of the invention is of particular usefulness where the cavity wall is the esophageal wall and the lumen is the esophageal lumen, in regions along the whole length of the esophagus. This is because the esophageal lumen, compared for example to the stomach, has exposure to an especially wide variety of body fluids during a healing process. However, the liner device is potentially useful in other lumens, especially when they are non-secretory.

The lumen liner is a simple device e.g. a disk, membrane, or patch, or a barrier that may be tubular or partially tubular. Said liner device allows the acute or immediate, subacute or delayed, chronic or recurrent passage of instruments, drugs, material or the like from outside of the body into an organ, space, body lumen or body cavity, through a passage in said liner. This means that the liner can be removed immediately after single procedure(s), or can be left for a period of time and then removed (or allowed to degrade in situ), or it can be permanently implanted to the wall of the luminal body organ or cavity for continuous use.

Figure 1:
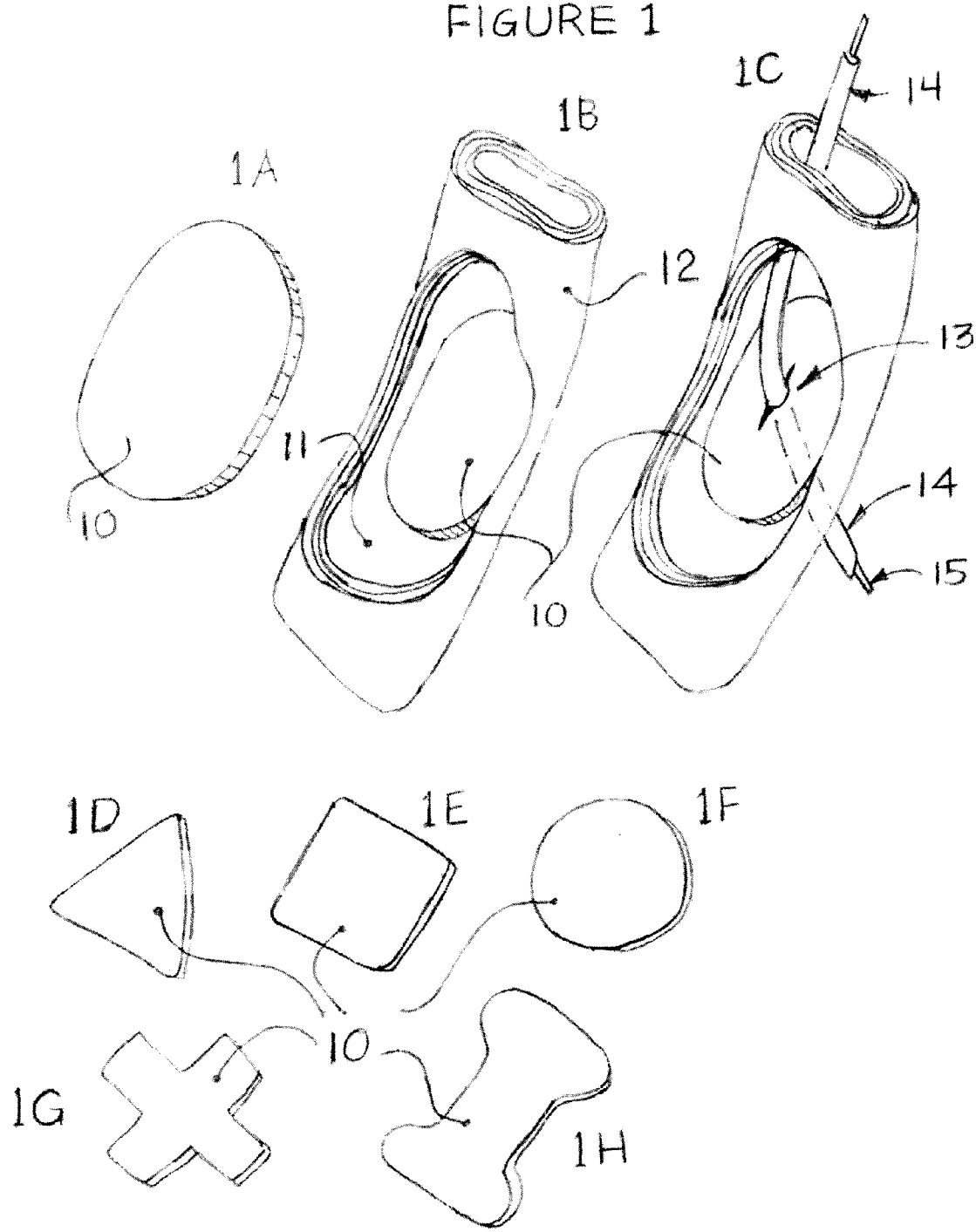
FIG. 1 shows a basic liner of the invention.

A simple liner device is shown in FIG. 1. As shown generically in FIG. 1A, a liner 10, which can also be called a membrane, a shield or a patch, can be a planar material. FIG. 1B shows the liner 10 of FIG. 1A liner applied to the interior wall 111 of a lumen 12, such as the esophagus. The liner is typically placed as shown in FIG. 1C to cover a site at which the lumen 12 is to be perforated by a device 14, most commonly from inside the lumen as shown at 13, but optionally from the outside or both sides (not illustrated here), which may require separate inside and outside liners to be attached. The catheter may carry a needle 15 or other penetration aid. The liner can have any shape, some of which are shown in FIGS. 1D-1H, including circular, triangular, rectangular, irregular, square, or generally any flat design. The liner can be double layered, having two opposing membranes that cover the wall at the same time (not illustrated).

Figure 2:
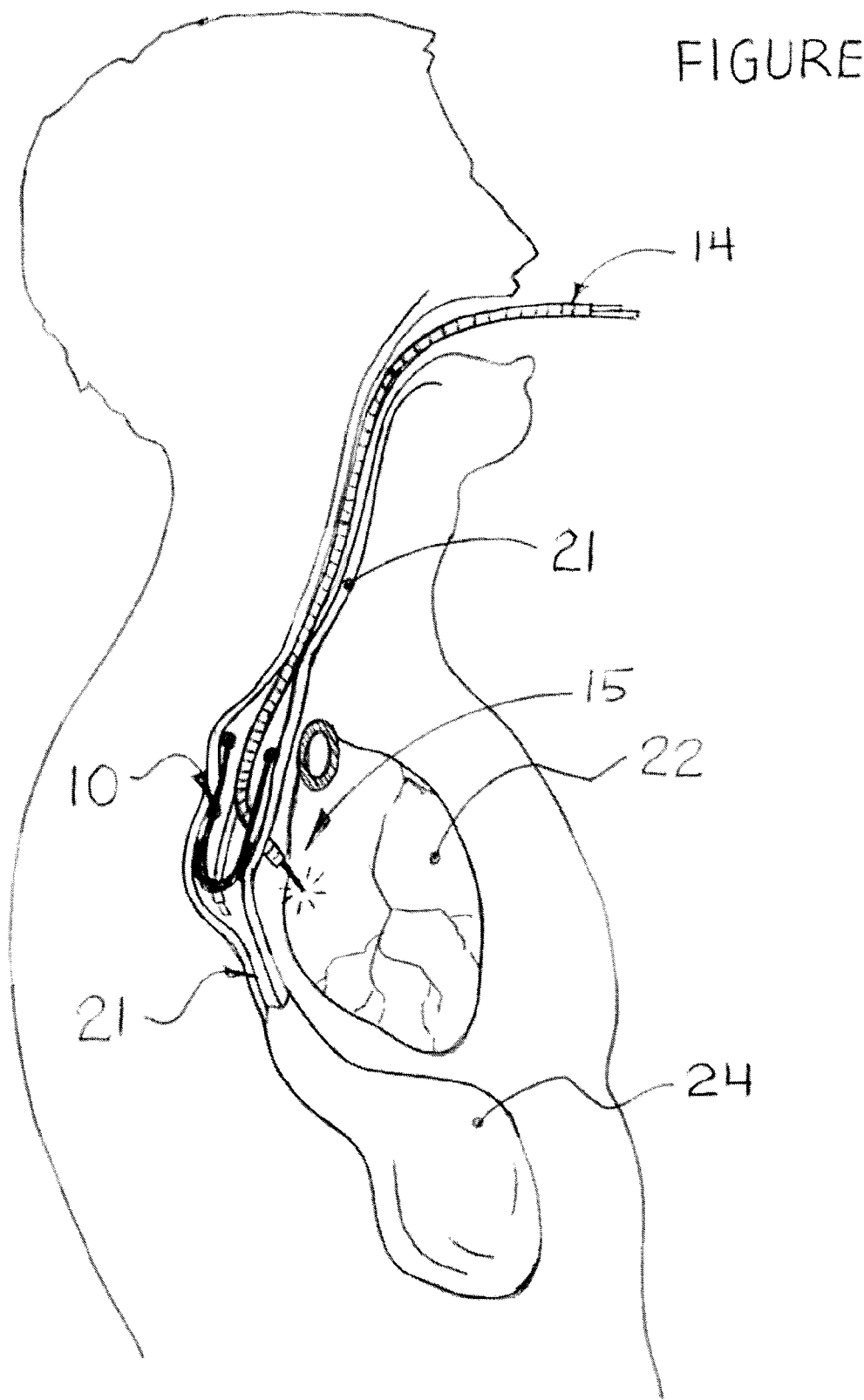
FIG. 2 shows a liner placed in the esophagus, with a catheter penetrating the liner for therapy on the heart.

FIG. 2, a schematic cross section of part of the human body, shows how a liner is used in a medical procedure. A depositing catheter (not shown) deposits a liner 10 in the esophagus 21 near the posterior side of the heart 22, and above the stomach 24. The depositing catheter is withdrawn, and a second catheter 14 is inserted through the esophagus 21 to the liner 10. A needle 15 is extended out of the catheter and through the liner 10, and penetrates the posterior side of the heart 22. Any of a variety of procedures can be performed, including for example electroablation of arrhythmia-causing tissue. In contrast to NOTES-type procedures performed through the stomach, the approach of the present invention is more direct, and does not require the penetration of the diaphragm, or the stilling of natural breathing, in order to perform certain cardiac procedures.

Figure 3:
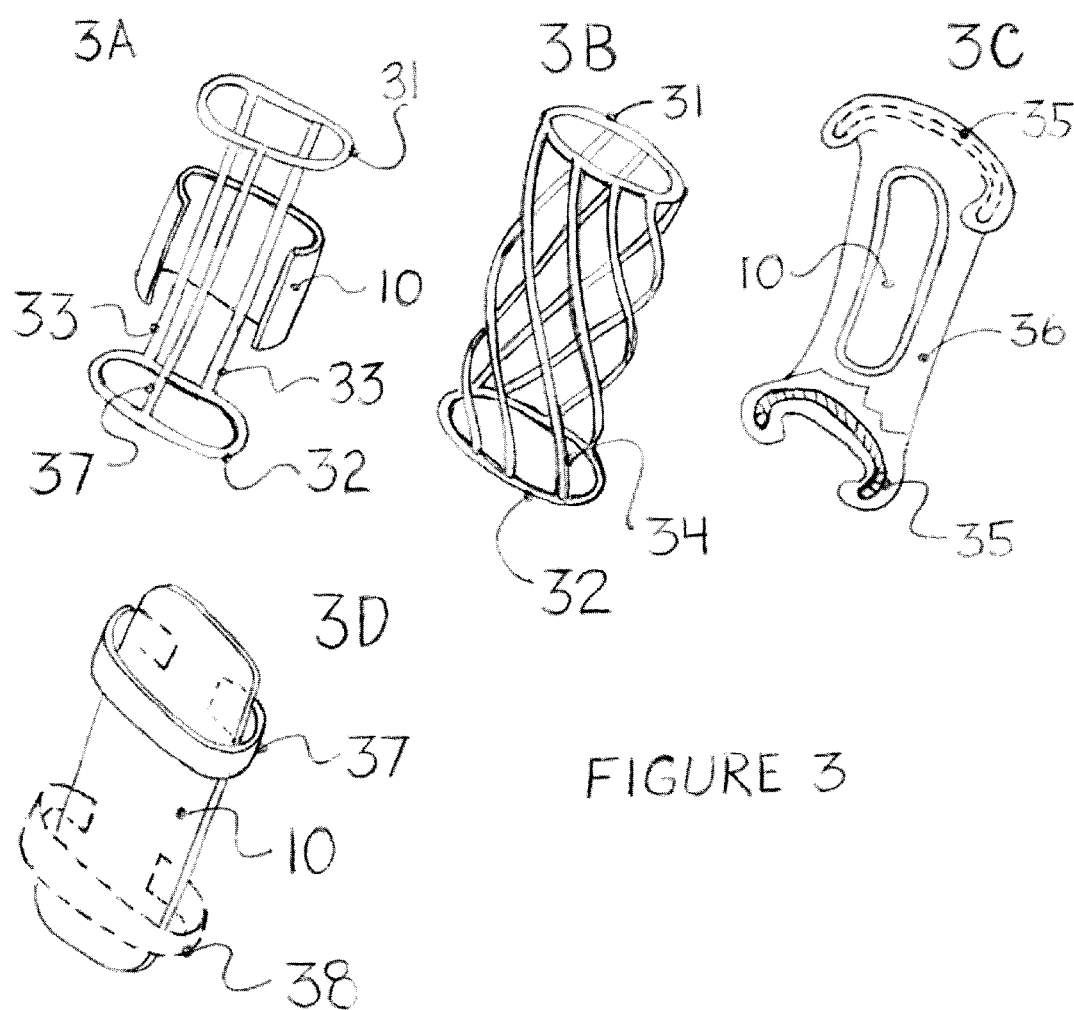
FIG. 3 shows a liner held in place by a frame.

The liner may be held in place, and/or held in a particular position, by a frame, as shown in FIG. 3. In one embodiment, shown in FIG. 3A, a liner 10 is attached to a framework generally shaped like the esophageal lumen, comprising hoops 31 and 32, and connecting pieces 33. The frame and the liner can be retrieved at the end of a procedure. Alternatively, the liner, or both the frame and liner, can be made of biodegrading materials that will spontaneously disappear after completion of local healing. FIG. 3B shows a meshwork of connectors 34 connecting hoops 31 and 32 to form a tubular enclosure, to which a liner can later be attached (not illustrated.) FIG. 3C shows a liner 10 carried on a fabric or mesh 36; the fabric is held in place by partial hoops 35. FIG. 3D shows a band 37, and a liner 10 which is placed so that a band 37 keeps the esophagus patent at the site. An optional second band 38 is shown in a dotted outline. A frame may also be used to produce a two layered liner, with an interior space, optionally filled with a foam or other filling.

Figure 4:
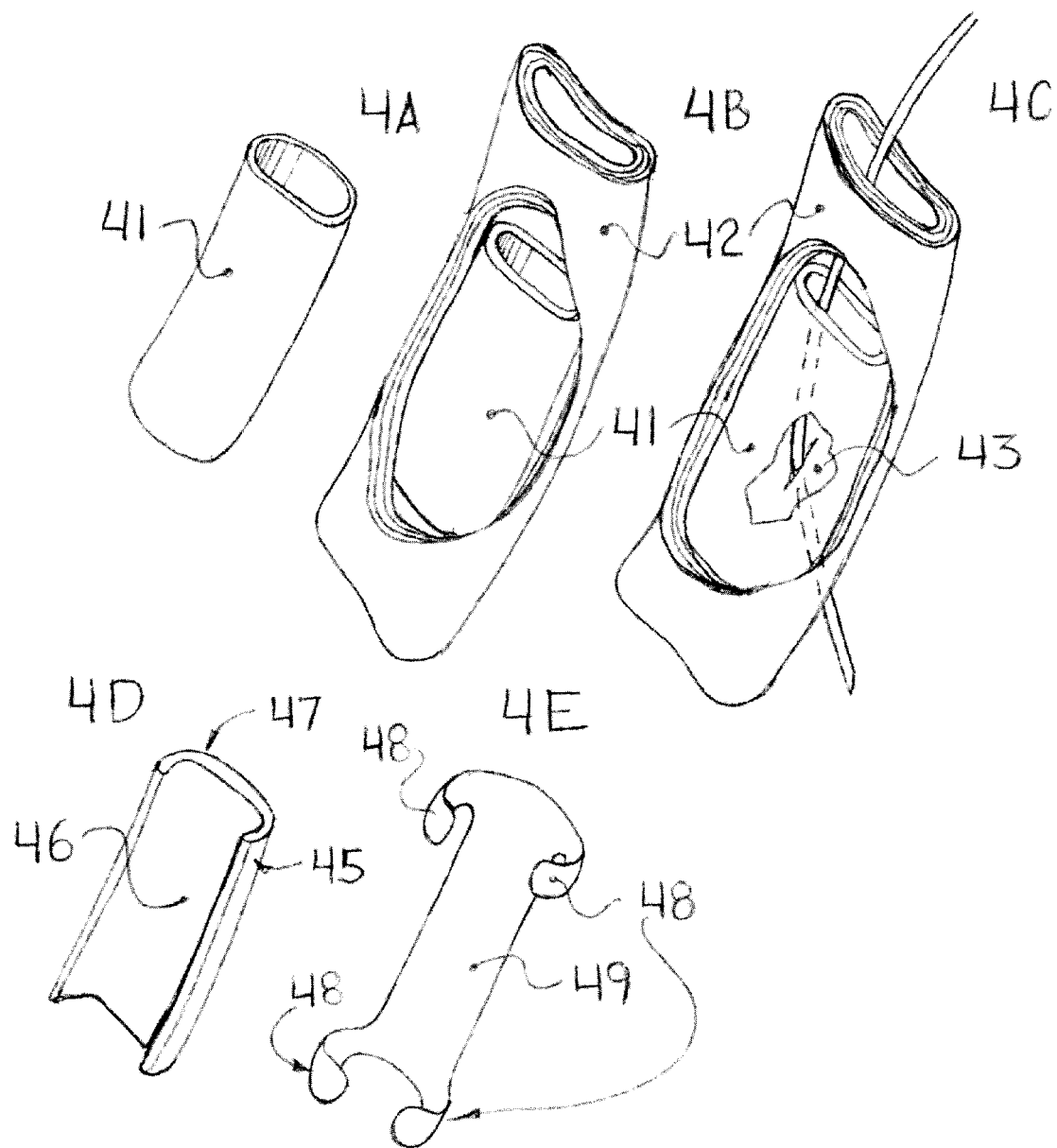
FIG. 4 shows a tubular liner and its deployment.

In another embodiment, the liner can be tubular, covering the entire inside of the esophagus or other lumen at a site; or it can be partially tubular, with complete tubular sections and other sections that do not cover the entire circumference. Some embodiments of tubular liners are shown in FIG. 4. A basic tubular liner 41 is shown in FIG. 4A, and the same liner 41 is shown inside the lumen of the esophagus 42 in FIG. 4B. FIG. 4C shows a slit at 43 in liner 41, through which a catheter 14 penetrates. A tubular lumen can be implanted as shown in FIG. 4D as a double layer, with one section 45 pressed against the wall of the esophagus, another section 46 being exposed to the interior of the esophagus, and so providing a potential pathway between these layers, for example at point 47. If the liner has some intrinsic stiffness, it can be shaped to hold a position in the esophagus as shown in FIG. 4E, with projections 48 to help hold location, and a general liner location at 49, which may be single layered as in FIG. 1 or double layered as in FIG. 4D. Such a double-layered structure can be used enhance self-sealing after removal of a penetrating device. For example, the space can be filled with fluid, such as a foam, and/or with a viscous, slow-setting adhesive material, before or after implantation. When a device is pushed through the liner, the foam can prevent leakage through the resulting hole during the procedure. When the device is removed, the fluid can rearrange to fill the space occupied by the device, and can set so as to prevent any fluid passage.

Fasteners may be used to retain a liner at a location, as illustrated in FIG. 5. In a first embodiment (FIG. 5A), a fastener 51 is retained at a site by an application of adhesive material 50 to the site. In embodiment 5B, a variety of standard fasteners are used to affix a liner 51 to a site, including a bent pin 52, a screw-in helix 53, and a hook 54. In FIG. 5C, a bent needle 55 affixes a liner 51 to a tissue site, and a thread 511 allows subsequent removal. In FIGS. 5D and 5E, a fastening system is shown in perspective and cross section, comprising a deformed disc 58 having an optional preformed slit 591; an affixing ring 57 with teeth 59; and a manipulation device 56 which can adhere to disc 58, for example by vacuum, and guide a catheter or other instrument to the site.

Figure 6:
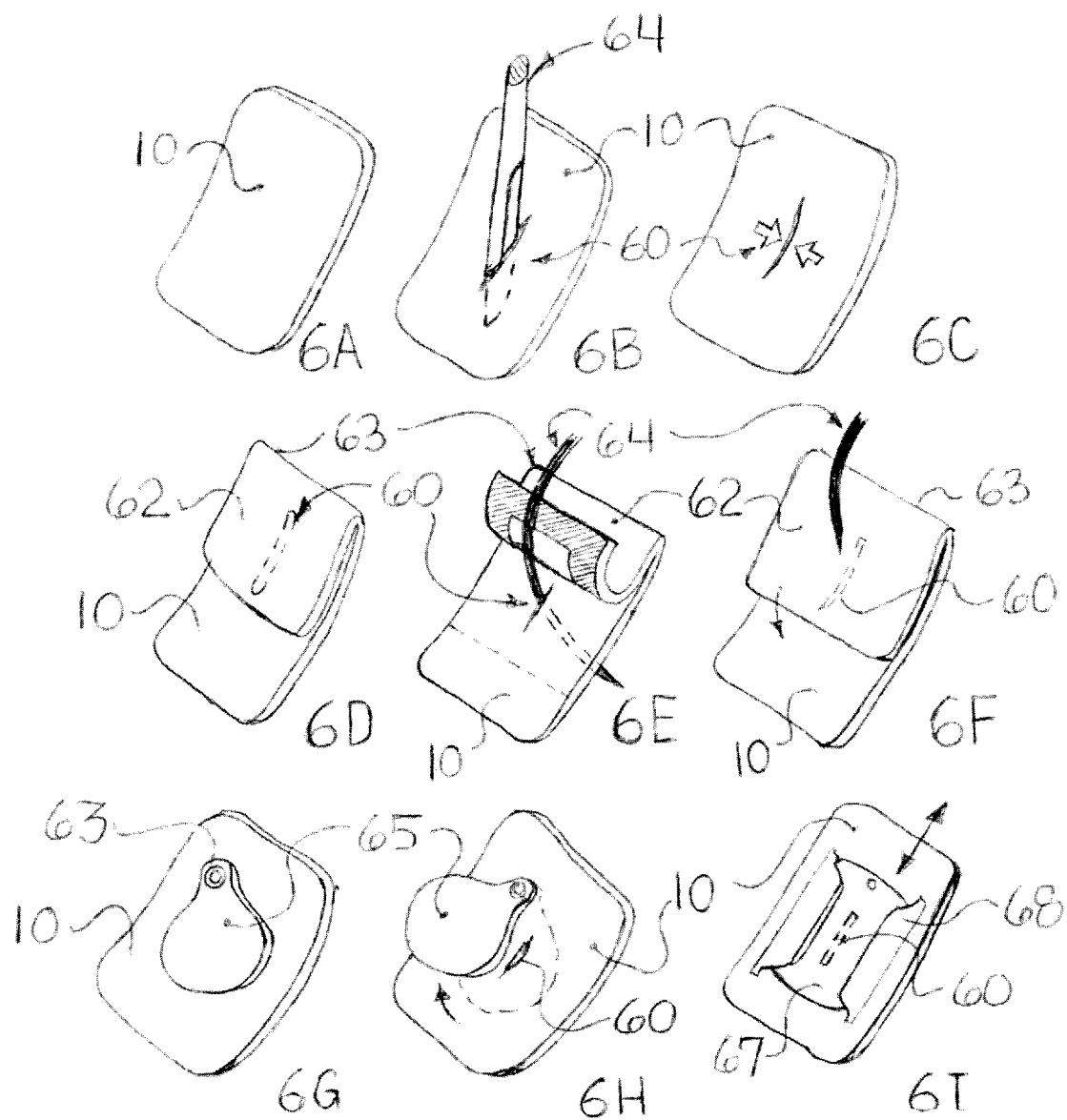
FIG. 6 shows means of closing openings through the liner to prevent leakage of fluids.

FIG. 6 illustrates some means of closing openings created in a liner. Liner 10 is shown intact in FIG. 6A, and is affixed to a tissue site. In FIG. 6B, a slit 60 or other opening is made in liner 10 and a device 64 is passed through the opening 60. In FIG. 6C, the device is withdrawn, and the opening 60 is substantially or completely closed (as indicated by opposing arrows) by resilience of the liner 10. In FIG. 6D, a slit 60 in a liner 10 is covered by a flap 62, which is affixed at its upper edge 63 to liner 10 or to another locus. In FIG. 6E, the flap 62 is pulled back sufficiently towards its upper edge 63 to expose slit opening 60, through which an instrument 64 is passed. In FIG. 6F, first the instrument 64 is removed (note upward arrow); then the flap 62 is closed, as indicated by an arrow, closing slit 60 and minimizing or preventing fluid passage therethrough. FIG. 6G shows a liner 10 with a slit cover 65 affixed to liner 10 by a connection 66, which permits rotation of cover 65 around connector 66, for example a rivet or other fastener. In FIG. 6H, the cover 65 is rotated and exposes a slit 60. An instrument can be passed through slit 60 (not illustrated), and then removed, and the cover 65 can be restored to its original position, preventing leakage. In FIG. 6I, sliding cover 67 is retained on liner 10 by retainers 68. The sliding cover can be moved (as shown by a double headed arrow) so as to obscure slit 60 and minimize passage of fluids through it, or to expose slit 60 for instrument passage.

FIG. 7 illustrates the use of valves more complex than a slit. Such valves can potentially achieve better controlled or more reliably closed action than a simple slit, although requiring somewhat greater complexity. In FIG. 7A, liner 10, positioned at the site where passage through the esophageal wall is desired, has a iris-type valve 70 mounted on it. In this embodiment, the valve 70 is operated by a remote connection 71. In FIG. 7A, the valve 70 is closed. In FIG. 7B, the valve 70 is partially open, in the center of the iris at 72. Other valve types besides iris valves can be used in such a system.

FIG. 7C shows a valve arrangement which can close or open two passages by movement of a control linkage from a remote site. Liner 73, which may be double walled like liner 41 of FIG. 4, is shown in place in the esophagus (which is not illustrated). Liner 73 has an upper insert 74 which blocks the passage inside of liner 73, and also contains two passages 75, for example for fluid, or for instrument passage or other purposes. These passages 75 emerge from the side of the liner 73 at 75*bis*. A control element 76 can rotate a wheel 77 about an axis 78 that is perpendicular to the wheel 77. This moves a set of holes 79, which lead to passages through the wheel 77, into or out of alignment with the external passages 75, thereby opening or closing the passages.

Figure 8:
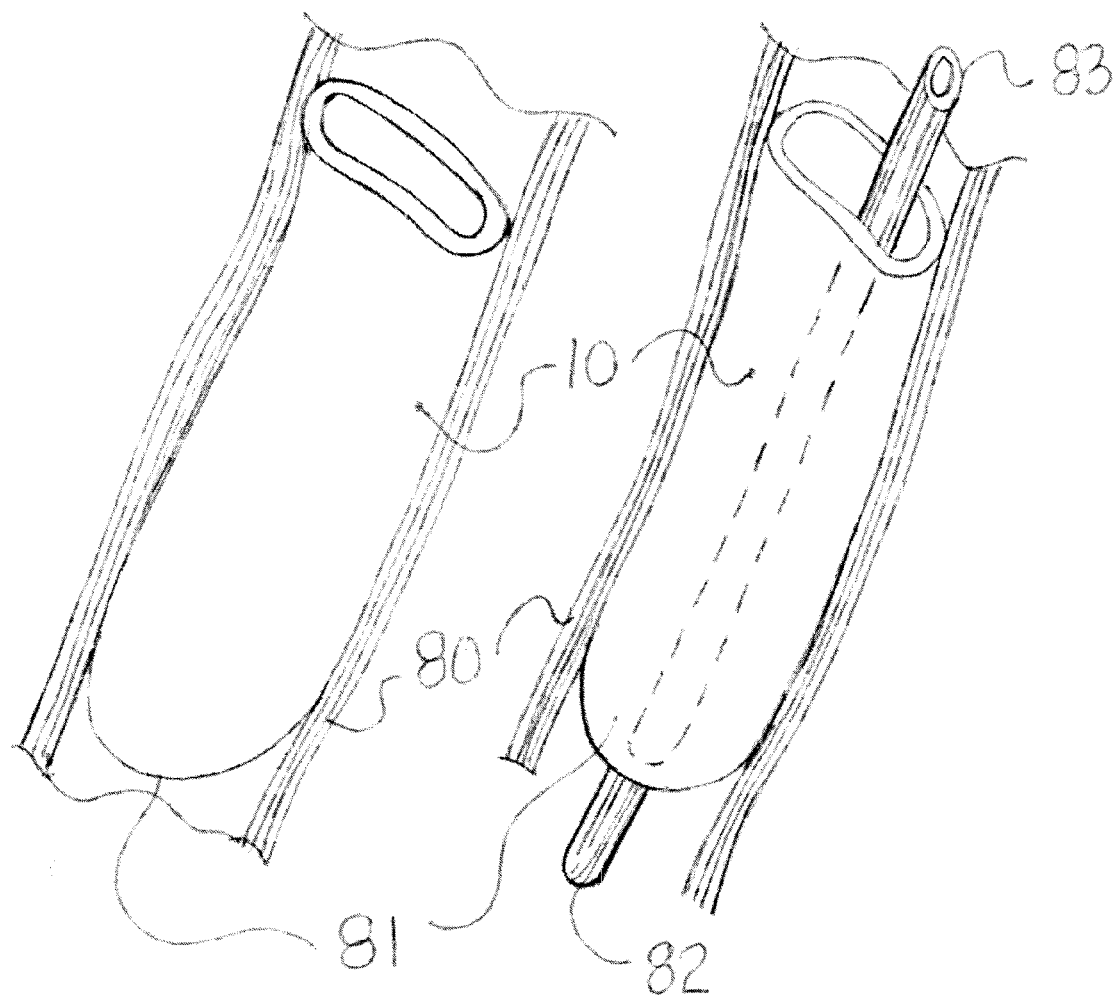
FIG. 8 shows a liner with a closed distal end, optionally with a tube passing through said distal end for other procedures.

FIG. 8 shows options for the distal end of the liner 10. In one embodiment, the liner 10, which is generally in contact with the esophageal tissue 80, is closed at its distal limit 81. In another embodiment, not illustrated, the distal end 81 is open. In another embodiment, the distal end 81 is pierced by one or more passages 82, which will typically have a distal end 83, through which fluids, sampling devices, and the like can be passed.

Figure 9:
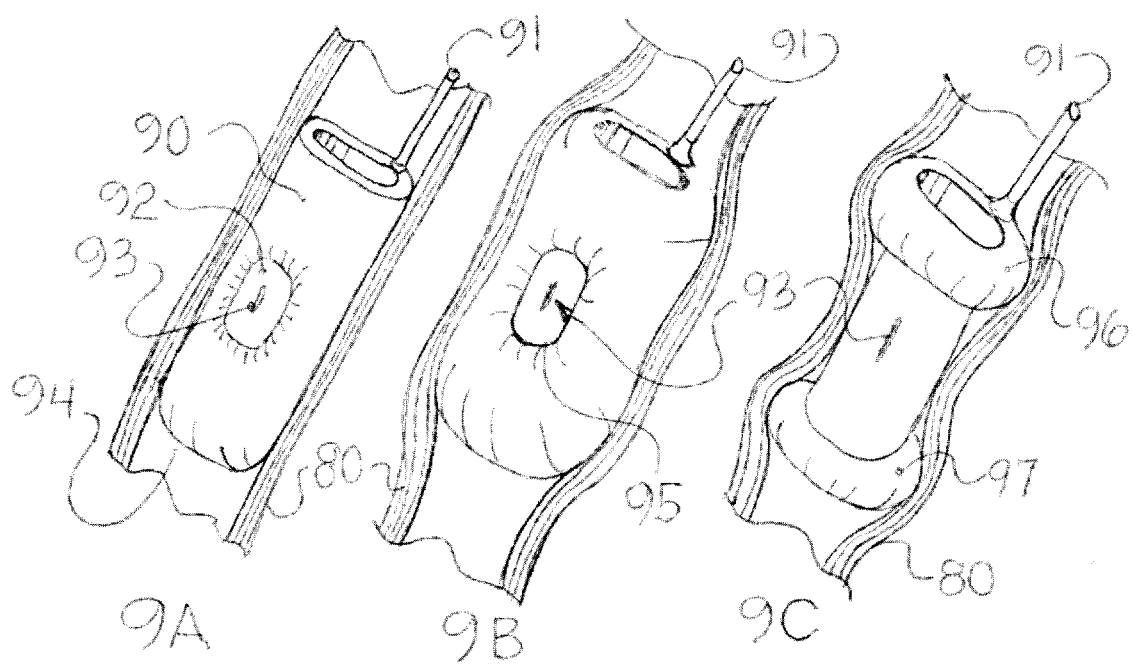
FIG. 9 shows inflatable liners.

FIG. 9 shows some of the uses of inflatable balloons for controlling position and passage in devices of the invention. In FIG. 9A, a double-walled liner device 90, located at a target site in the esophagus and contacting the esophageal wall 80, has a connection 91 to a source of pressurized fluid, and a passage route in its side having a valve area 92 comprising a slit or other closeable opening 93. The distal end 94 of the liner device 90 is typically closed, as illustrated, but such closure is not required. When the device 90 is inflated with pressurized fluid, as shown in FIG. 9B, the esophagus is locally distended, and a port area 95 is created on the lumenal side of opening 93. This provides maneuvering room for passage of an instrument through the opening 93 with proper alignment, and completely seals the area against fluid bypass.

FIG. 9C is arranged somewhat differently, and pressurized fluid injected through tube 91 inflates an upper balloon 96 and optionally additionally, or instead, inflates a lower balloon 97. This confines any leakage through opening 93 to a limited space.

Figure 10:
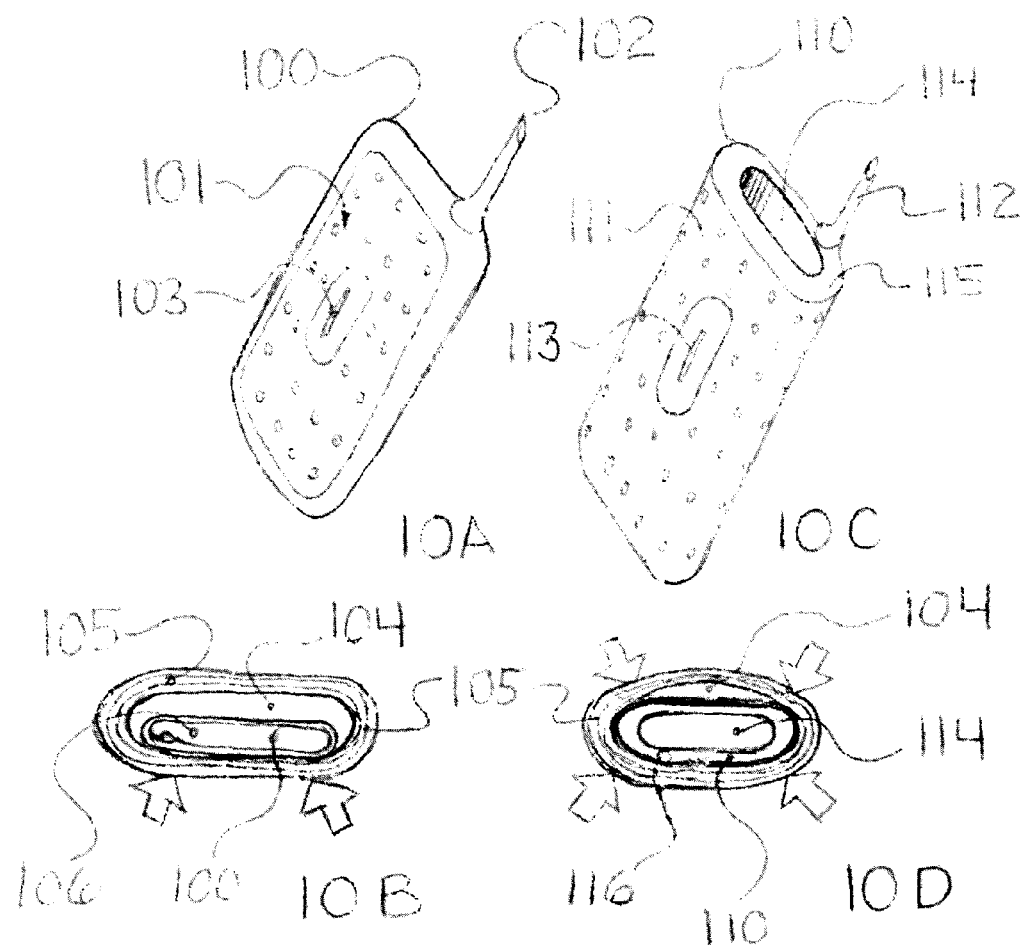
FIG. 10 shows liners with vacuum-assisted adherence to a lumen wall.

In FIG. 10, a double layered liner 100 with a space between sealed-together layers has a first side that is perforated and connected proximally to a vacuum source, directly or otherwise, to allow its controllable and reversible affixation to a wall of the esophagus or other targeted tissue. In FIG. 10A, a generally planar double-layered liner 100 has vacuum holes 101 on one side, and not on the other side (not shown), and has a connection to vacuum at 102. A slit or other port 103 is disposed in the vacuum side of the liner. In cross-section 10B, the wall 105 of the esophagus is shown, as well as the interior space 106 of the liner 100. Likewise, in FIG. 10C, a tubular liner 110 has vacuum ports in its outer wall 111, and not in its inner wall, and a vacuum connection via hose 112 to its inner volume 116. The tubular liner 110 has a central space 114, seen in FIG. 10D, while the planar liner 100 leaves an open space 104 inside the wall 105 of the esophagus. With either device, application of vacuum at the port 102 or 112 will firmly and reversibly affix the liner to the wall of the esophagus, allowing passage of instruments through openings 103 or 113 without significant leakage of fluids into other compartments. The liner device is then easily removed by relieving the vacuum, and withdrawing the liner, for example by the vacuum connection.

Figure 11:
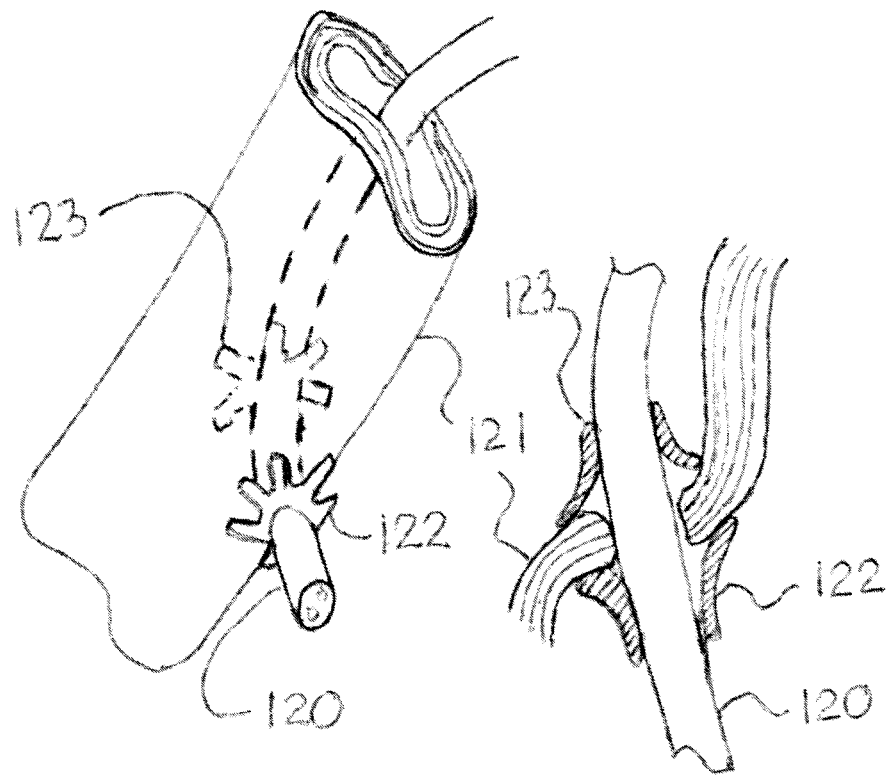
FIG. 11 shows liners on both inside and outside surfaces of a lumen.

FIG. 11 shows two views of a catheter 120 penetrating the esophageal wall 121 and having liners 122, 123 as sealing elements on both sides of the wall 121. The liners can be designed so that their openings close upon removal of the catheter.

Figure 12:
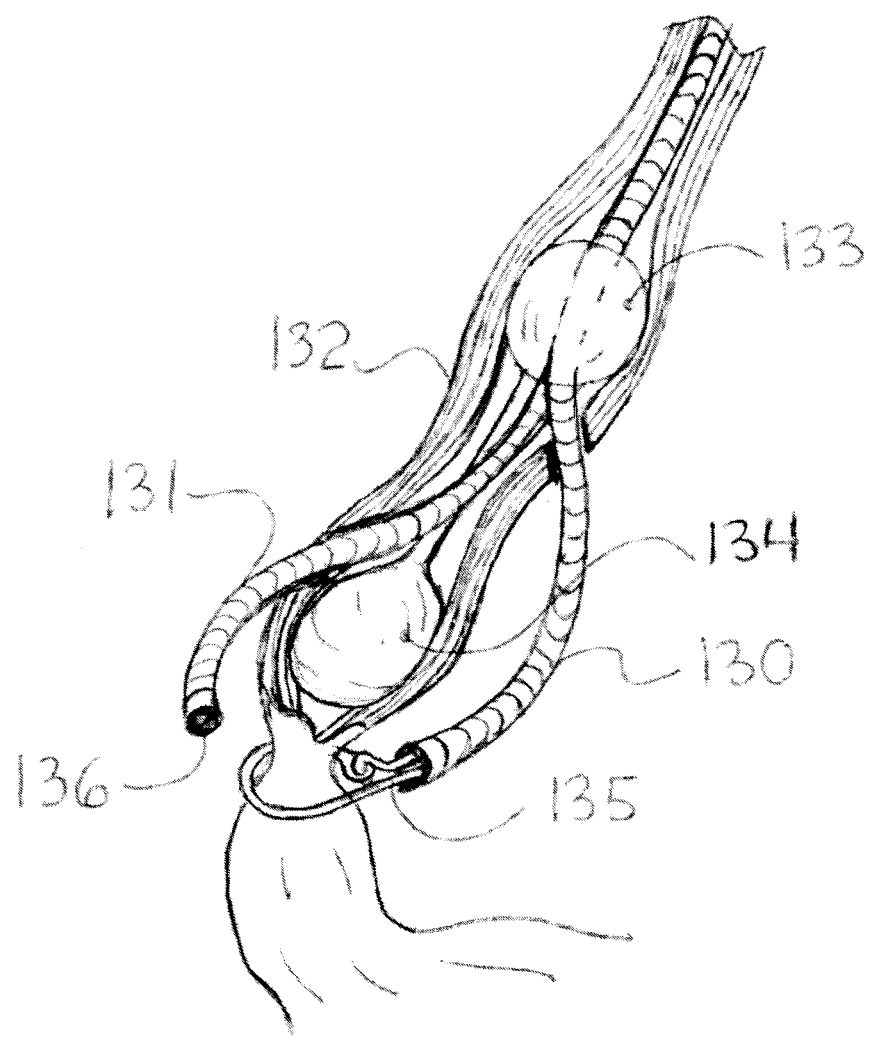
FIG. 12 shows a procedure using two openings.

FIG. 12 shows two catheters 130, 131 emerging from slits in the wall 132 of the esophagus. The emergence slits lie between sites of occlusion of the esophagus, 133 and 134, which may be provided by an inflatable device like the one shown in FIG. 9C, or by other means. The first catheter 130 carries a detachable snare 135, which has been closed around the esophagus 132 to limit the diameter of the esophagus, for example to decrease the speed of eating by a patient. The second catheter 131 carries illumination and viewing means operating through its tip region 136, allowing observation of the process of setting and sizing the loop of the snare 135. FIG. 12 illustrates the importance of being able to control the direction in which a device penetrates the esophagus, and the utility of kits providing for two or more devices to be operated simultaneously.

Figure 13:
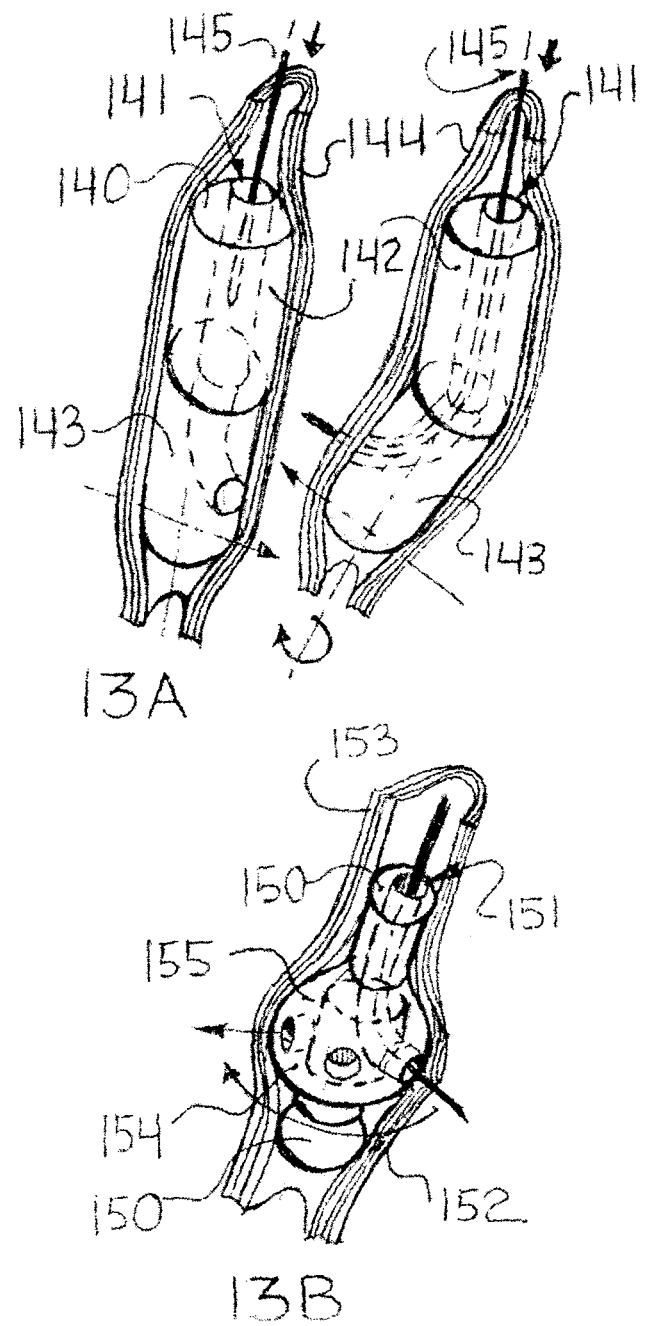
FIG. 13 shows methods of steering a catheter or other device.

FIG. 13 shows devices with a steerable exit port. In FIG. 13A, a first embodiment of a generally cylindrical lining device 140 having a central lumen 141 is provided in two sections, upper section 142 and lower section 143. The device is delivered to a section of the esophageal lumen 144 at which a port is to be created. A wire 145 or other control means can rotate the lower section 143 of the device with respect to upper section 142, thereby controlling the position at which a catheter would penetrate the lumen wall 144. If the plane between section 142 and 143 is inclined, as illustrated, then a rotation will also cause a local bending of the esophagus, and control the angle as well as the rotational position at which a device will emerge from the lumen 141.

A different embodiment, shown in FIG. 13B, has a device 155 with upper and lower inflatable balloons 150, and a center passage with an inlet at 151 and a rotatable outlet 152 which can allow access through the lumen wall 153 at various rotational positions, through various outlets in the lower section 154 of the device.

Figure 14:
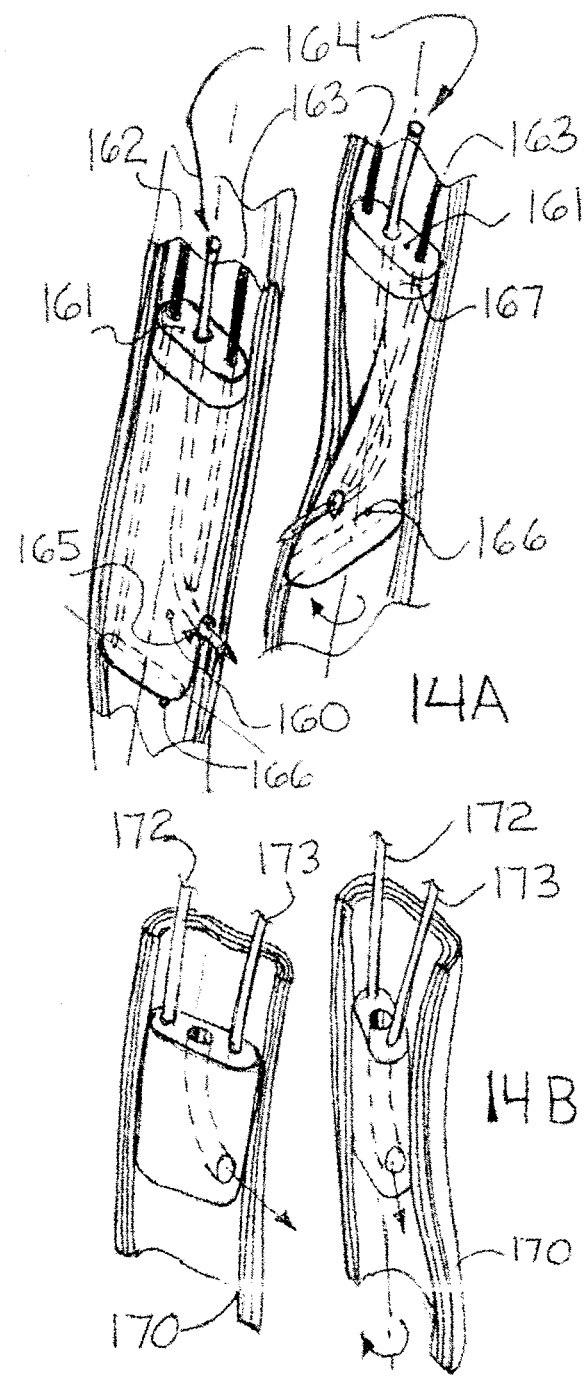
FIG. 14 shows additional steering methods.

FIG. 14 shows alternative means of selecting the rotational position of exit of a catheter or other device through the wall of the esophagus, by rotation of the esophagus itself. In a first embodiment 14A, a liner device 160 has a rigid upper section having two control wires 162, 163 and an entrance port 164 and exit port 165 for a catheter or other device. By applying torque to the device via the control wires 162, 163, the distal end 166 of the device will rotate with respect to the proximal end 167, allowing control of the exit direction of a device passing through the entrance 164 and exiting through exit 165. In a second embodiment 14B, a liner device 171, similar to the liner in FIG. 7C, is placed in the esophageal lumen 170. Application of twisting motion to control wires 172, 173 can twist the liner, and with it the lumen, to allow emergence of a catheter or other apparatus at a desired rotational angle with respect to the patient's body as a whole.

Figure 15:
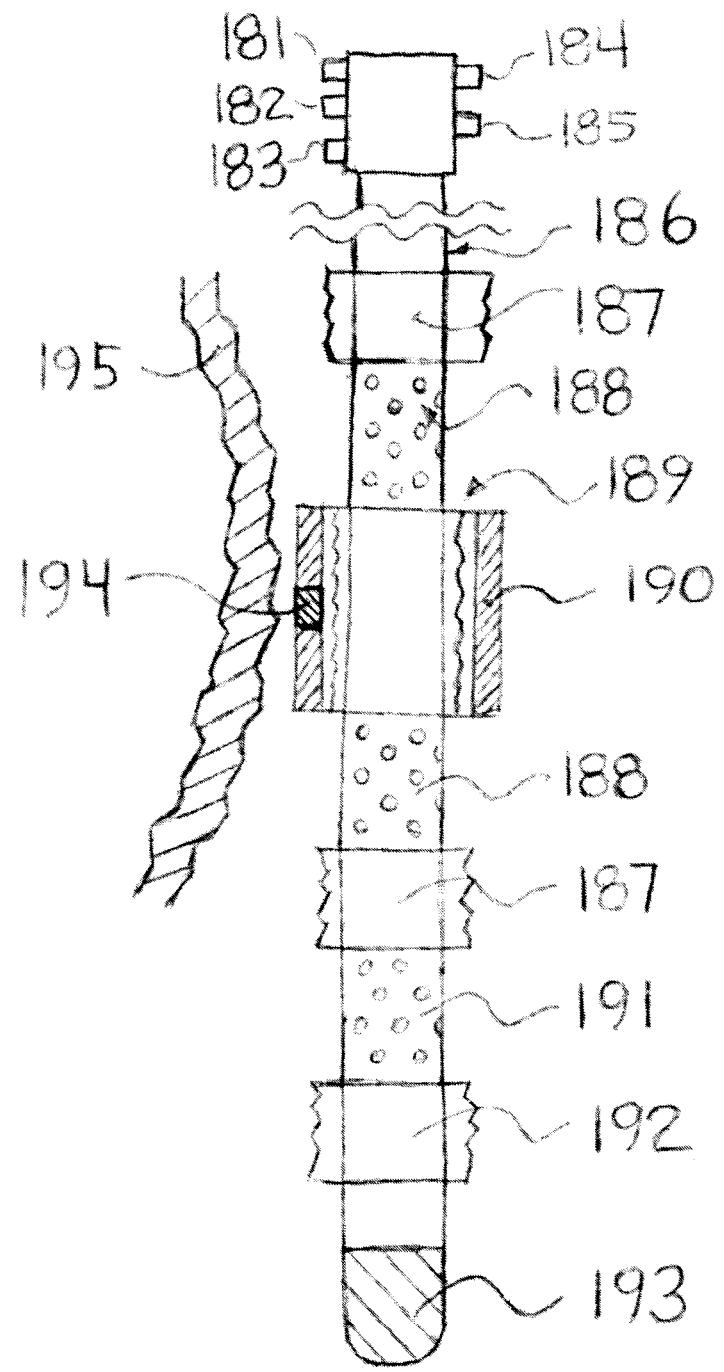
FIG. 15 describes an integrated deployment device for use in the invention.

FIG. 15 shows a particular complete deployment device or integrated of the invention, and is described in more detail below.

Uses and Other Aspects of the Invention

The liner can be used to facilitate surgical procedures through the wall of a luminal structure or body cavity wherein said procedures can be conducted either with removal of the tubular liner device or self absorption, for example within 36-48 hours after the procedure. Or, the procedure can be sub-acute placement to allow for a planned second operative step or a redo; or it can be a chronic (long term) placement as a launching station to the neck compartment or the thoracic cavity to deploy pace makers or batteries, to perform various diagnostic and therapeutic procedures via endoscopy when the scope interrogates an embedded intramural ring, which may itself be a part of the original liner device that did not degrade after implantation of the liner.

The liner device may be made of a sterile, antiseptic and/or antimicrobial material. The material of the liner may be a solid; or may be a foam, or a layered foam, or a spreadable separator material, applied by painting, spraying or layering of a semisolid or foamy state of an applied material to cover a perforation site in the wall of the luminal organ or cavity.

Moreover, the semisolid or foam layer may have a pre-manufactured flap or valve positioned around a pre-made hole in the layer to allow for passage of endoscopes or other devices. In some embodiments, a foam or semisolid layer later collapses on itself and seals any hole made through said layer during the passage of instruments, and so obviates the need for a pre-manufactured hole for passage of said instruments.

Likewise, a material in a fluid state or semisolid state, which adheres to some extent to an elastic membrane or sheath, can be coated onto the elastic membrane and lined with or covered with another layer of elastic membrane or sheath, providing support on both sides of the fluid or semisolid layer, thereby constituting a triple layer liner device structure made of two layers of sheath filled with fluid and/or foam in between said layers. This type of triple layered structure can have a pre-manufactured hole across the three layers to allow for passage of instruments. The presence of a fluid or foam layer as a middle layer between the outer two layers of the sheath can seal off the communication between said sheath layers after withdrawal of instruments.

In another type of a triple layer design liner device, a liner can have two un-aligned pre-manufactured holes, one hole in the internal layer and the other in the external layer, but not aligned with each other, so that the scope or tubular instrument passes across the liner triple layer device in a zigzag fashion which seals off the holes against each corresponding wall after withdrawal of instruments.

Similar results can be obtained by using small patches, carried on an endoscope or other instrument (not illustrated), which have asymmetric holes in their surfaces, and which can be induced to oppose each other during the course of withdrawal of an instrument. In general, the liner can be sealed whenever two layers of membrane, disk, patch or barrier oppose each other, for example slideably with respect to each other. The sliding of the components can align two holes (one on each layer) so that they are together (open position), away from each other with no overlap of the holes (closed position) or with partial overlap of the holes (partially opened/closed). The exact shape of the components is not critical. Such a liner device can isolate a partial or full thickness perforation in the wall of a lumenal body structure or a body cavity from inside, outside or both sides. The isolation of the perforated portion of said wall allows the perforation to heal while the liner device prevents direct communication or contact between the perforation site and the lumen of said organ or cavity and/or its surrounding structures from outside. Said liner prevents contamination of perforation site by covering it and keeps the perforation edges sterile until healing occurs spontaneously or by mechanical approximation of edges of said perforation. The liner device may be a complete or incomplete cut section of a tubular device, as well as planar. The devices may adhere to the lumenal wall by any of the mechanisms discussed above (adhesives, pins, inflatables, etc.).

In another aspect of the invention, a central pre-manufactured hole may be made to include a rotating or revolving mechanism with open, semi-open or closed phases. For example, a device may be made of two successive linear disks, membranes, patches or barriers, wherein each linear device of the two has a hole in its wall to allow for the passage of instruments, but wherein said holes are not aligned across from each other in the plane of the device. Later, the withdrawal of the instrument from the device creates an opposition of the two components, disks etc of the liner device, in a way that seals the hole on each wall by closing it against the other wall (versus against the other hole). Where this is arranged, clearly the exact shape of the membranes is not critical, and need not match exactly, as long as the separated holes do not face each other after the procedure is completed.

A preferred embodiment has a first layer with a side opening and an overlying second layer with a second side opening on the wall. When the two tubes slide on each other, the two side openings can be aligned into one opening (open position) or can be aligned away from each other (closed position) or a position in between (partial opening).

The invention also includes the case in which the liner device is a vertical sheet attached to the wall of a luminal body structure or body cavity along its longitudinal axis. For example, said vertical sheet, which may be square, rectangular, irregular or other convenient shape in two dimensions, typically has upper and lower ends. In some embodiments, illustrated in FIGS. 3 and 4, each end of a vertical sheet or a patch may have a U-shaped transverse collar running around the interior or exterior wall of the lumen and holding the liner against the lumen. Such collars can fix the liner device to the wall from inside, outside or both sides. The vertical sheet may have at least one side opening to allow passage of devices. The side opening can be fitted with a valve mechanism as described in FIG. 7. An adhesive may be used to adhere the device to a lumen wall, or vacuum can be used as shown in FIG. 10.

Generally, any part of a liner device can be used to fix the liner to the wall of said lumenal organ or cavity e.g. with glue, hooks, pins, spines, balloons, collars and the like. There may also be only one collar, attached to only one end of a tube, sheet or patch, the whole device attached to the wall of the lumen by the above means.

In some embodiments, the liner may be supplemented or replaced with one or two end plates, which span the lumen and block it off. Each plate may have a central hole for passage of devices. An example of such an embodiment is seen in FIG. 14. The plates, which may have self-closing slits for passage of devices such as an endoscope (not illustrated), isolate the target segment of the lumen from either or both ends against secretions, leakage or contamination. The plates may be made of materials similar to the liners described previously. The plates may be affixed to the walls of the lumen by means such as those recited above.

In another embodiment, the liner device has a valve mechanism on or connected to a hole (for example, a slot in a rubbery liner septum) to allow for passage of surgical devices or scopes through the valve mechanism and across the perforation in the wall, while having the opening be self sealing against fluid passage. (See FIG. 7, for example.) The liner, as described above, may seal a perforation in the lumen wall by directly blocking fluid passage. In addition, or instead, flow of fluid and passage of instruments can be accommodated and reversibly blocked by a side opening mechanism, or "SOM". The SOM is a device that can be attached to a liner, or itself be a liner, which device has means for reversible closure. An example of a valve-type SOM is sown in FIG. 7. Any device can be used that is operative in this fashion, including, without limitation, a shutter that moves up and down, side-to-side or diagonally with respect to any barrier; a pair of shutters moving away from or towards each other; simple or double flaps; a hinged door mechanism; a fitted stopper; an iris; a zipper; and the like. An iris-like SOM is used in the Figures to indicate any of these options. In addition, while a SOM is generally illustrated herein as attached to a liner having greater area, the liner, patch or sheet may be reduced sufficiently, or eliminated, so that the SOM is effectively or actually adhered to a location where a hole is to be made, without requiring an additional liner, patch or sheet element. As illustrated, a SOM will usually have a control means operable from outside the patient, or by remote means. The SOM may be affixed to the wall of the lumen by vacuum, as shown schematically in FIG. 10 for liners.

Closure can also be achieved by other methods, including without limitation applying a one-layer device; conducting a procedure; and covering the hole in the device with an adhesive patch ejected onto the site by an endoscope or other delivery device (not illustrated.)

As an example of how a liner may be delivered to the target site on an endoscopic instrument, a tubular liner device may be delivered to a target segment in the esophagus by being secured on an endoscope, with or without a side-viewer eye for placement. The scope segment that carries the tubular liner preferably has an inflation mechanism to push the liner wall into the mucosa of the esophageal wall circumferentially with or without fixation mechanism. The scope segment carrying the liner can be transparent to allow for vision during placement. The transparent segment may have light/vision capability on the side wall of the scope or inside the scope lumen. This is especially helpful when the liner is also transparent.

The liner may comprise one or more chemically or pharmaceutically useful substance for absorption across the esophageal wall, or for direct treatment of the esophagus. The liner may also comprise valves to control the amount of material that can pass through the lumen where it is implanted. Such controls may operate either directly through the lumen, or as a regulated flow through the wall of the lumen. A liner may comprise a tubular structure in the form of a sterile elongated sheath that has an upper opening and a side opening. Each opening may have a valve mechanism (e.g., a funnel shaped valve or a SOM). The side opening may have a SOM, Instruments, scopes and devices can pass from the upper opening to the side opening, while covered by the sheath. The sheath can be filled with sterile fluid for sealing.

As another closing mechanism, a tubular double-walled liner may have two holes, an inlet hole and an outlet hole, for example one near each end of the tubular liner (not illustrated). The holes are not on the same vertical plane. Optionally, they are perpendicular to each other on a cross section prospective. Instruments pass from the inlet hole on one wall, and down the lumen of the tubular liner to come out from the outlet hole, before they reach the wall of the luminal organ (e.g. the esophagus) and come out from the wall penetration. The outlet hole is aligned with the wall penetration. The tubular liner is fixed opposite the wall of the luminal organ (esophagus) e.g. by glue. The lumen of the tubular liner is also lined with glue from inside. Once the instrument is withdrawn upon completion of the procedure, the outside wall of the tubular liner collapses against and seals the perforation in the wall of the organ; the inlet and outlet holes are sealed against an opposing wall of the tubular liner. The lumen of the tubular liner is obliterated after collapse of the two walls together and adherence to each other by means of the lumen-lined glue.

Other Deployment Mechanisms

Regular endoscopes can also be used to perform most surgical procedures suggested by the current invention as methods of transesophageal surgery in the neck and thorax. However, in another embodiment, a multifunctional, powered or non-powered, guide wire system with an array of functions, sizes and shapes is provided for use with the transluminal access system provided by the liner system. The invention teaches the use of the novel guide wire system with flexible functionality and smaller size compared to currently used scopes. These special guide wires pass through small penetration in the esophageal wall and reach target locations outside the esophagus in the cervical and thoracic regions. The system is applicable to other lumens and routes of entry into the body.

A scope with a side viewer may be used to deploy a tubular liner device. After the liner is securely fixed to the esophageal wall, a needle tip is used to make a partial thickness perforation in the esophageal wall. The perforation is dilated by blunt dissection (dilators) until full thickness perforation is achieved at minimal tissue damage. Such a system can take advantage of the protection provided by the liner system, while using a thin, minimally disruptive instrument for operating outside the confines of the esophagus or other access lumen. This reduces trauma and simplifies management of many procedures. For example, any of various ablation techniques can become simpler, more accurate and less traumatic.

Use of a Liner as a General Deployment Device

In addition to deployment of a liner via a scope, a deployment device or apparatus can be used as a means for placing a tubular liner at a target location on the wall of a luminal organ or cavity. The deployment device is a long, hollow, tubular structure that carries a tubular liner over its circumference at some location between its upper and lower ends. There is a circumferential balloon between the tubular liner and the wall of the deployment device (DD).

FIG. 15 is a diagram of a deployment device (DD). A deployment device will be tailored to a particular procedure, or to a family of procedures, and there will be numerous detailed arrangements. The arrangement of FIG. 15 is an example of the kinds of devices contemplated, and is not a limiting embodiment. In FIG. 15, the endoscopic deployment device 180 has five inlets or inputs: 181, optical and electrical connections; 182, vacuum; 183, spray for antiseptic or other fluid; 184, air for sealing balloons; 185, air for a deployment balloon for deploying a liner. The periphery of the device barrel 186 has segments 187 carrying a sealing balloon, 188 having vacuum ports, 189 comprising a deployment balloon for expanding to deploy a liner 190, the liner having a port region or other provision for an opening 194, against the inner wall 195 of the esophagus, and optionally at least one spray zone 191 for spraying an antiseptic or other fluid and optionally a further sealing balloon 192; and finally a segment 193 containing optical components, lights, ultrasound and other imaging equipment, and the like.

A deployment device will typically have at least three proximal ports, including a vacuum port, a liner balloon port, and a sealing balloon port. There are, in this particular embodiment, three sealing balloons, two vacuum port areas 188 to increase the degree of sealing, and at least one spray area 191, for example for dispensing antiseptic. Between the vacuum ports is a tubular liner 190 and a deployment balloon for the liner 189. There may also be a number of circumferential balloons above and below the liner. At least one balloon above the liner and/or below the liner can seal the lumen of said luminal organ when inflated in a donut shaped fashion. The balloon inside the liner pushes the liner towards the wall of the luminal organ upon inflation, and can push the liner's external wall into contact with the internal wall of the organ.

The deployment device may also have numerous pores. The pores may be continuous with an underlying space, or each pore opening or group of openings may be directly connected to a separate channel. In either case the pores, shown in segment 191, can be used to spray the internal aspect of the luminal organ with solutions or powdered materials. The sprayed material may comprise antiseptic solutions or cleansing solutions, for example prior to performing a procedure. They can also be used to apply vacuum to the wall of said organ when required for more secure isolation of the segment. It could be possible to improve sealing by alternating vacuum and pressure areas in any order.

Through the hollow core of the deployment device (not illustrated), medical and surgical instruments, including but not limited to endoscopes, ultrasound probes, suture devices, scalpels, lasers, grabbers, radiofrequency ablators, etc., can be passed from its proximal end outside the body to its distal end at the operation field. Such instruments and probes can also be used at points along the barrel of the deployment device. The deployment device may further comprise an inner sheath (not illustrated) that can be removed or stripped to expose a sterile inner surface.

The deployment device may be used to deploy a tubular liner in a patient prior to a procedure in which general anesthesia is not necessarily required. For example, in the case of the esophageal lumen, there are no pain receptors in the wall, and hence conscious sedation can be used during the procedure without having to put the patient to sleep or use intubation. In the case of an esophageal procedure a spot in the esophagus is identified by imaging or by ultrasound guidance. The deployment device with a liner 190 for implantation is introduced into the esophagus and situated so that the liner overlies this predetermined segment. The sealing balloons 187 of the apparatus are deployed, creating an enclosed space which contains the segment in which the port is to be deployed. Antiseptic is injected through special channels of the apparatus and is delivered to clean the area. Vacuum suction is applied to the channels to remove antiseptic and to create a tighter seal between the apparatus and the esophageal wall. The liner 190 is then expanded by its deployment balloon 189 to push the liner 190 against the esophageal wall 194. If desired, the liner may be attached to the lumen wall by additional means, as previously described. A transesophageal opening is created by surgical incision through the dedicated area 194 of the liner, which may be preceded or accompanied by the further addition of valve mechanisms or other accessories as described above.

Following the opening of a passage, procedures are performed, and then the instruments are removed; the port is sealed or the liner is allowed to close or assisted in closing; the balloons are deflated; and the deployment device is removed. The patient will generally be held for observation and to ensure stabilization of vital signs, but in simple cases, no further treatment may be required.

Example 1

Transesophageal Microaccess for Spine Treatment

Cervical and thoracic spine disorders are of special importance due to the complexity of the bony/cartilaginous structures in relation to the spinal cord. For disorders like cervical disk disease, the current surgical solutions are very complex and involve dissection through many layers of tissues, and affect many sensitive vascular, neurological or lymphatic structures before the surgeon is able to reach the target lesion in the disk area between cervical vertebrae. This applies to both the anterior as well as the posterior approach.

What is needed is a simpler, less invasive and more precise method to reach the cervical disk/vertebral lesion and related structures without the need to dissect through many tissue layers. The posterior "Transesophageal Microaccess" approach is described below. As will be shown, the access to the cervical spine through the esophageal wall is short, wide and relatively direct as the esophagus is directly related to the vertebral column posteriorly. The esophagus is cleaned by antiseptic solutions to decrease any amount of infectious agents in the surgical field.

The devices to perform the surgery include a deployment scope, a liner, an obturator, and a therapeutic scope or device. The deployment scope is the scope that carries the liner on at least part of its wall to be delivered to a target segment in the esophagus. In one embodiment of the invention, the part of the scope that carries the liner is transparent; in another preferred embodiment the liner itself is also transparent so that the esophageal wall can be imaged during deployment. There may be an external imaging device e.g. fluoroscopy, to direct the liner placement to a target area in the cervical spine. Once the liner is at the target location, the scope is rotated along its short (horizontal) axis to direct the side opening mechanism posteriorly to face the vertebral column at the level of the lesion. In a preferred embodiment there is an inflation mechanism between the liner and the carrying deployment scope that when activated can push the liner wall outward into the esophageal mucosa for fixation. In another preferred embodiment there is no inflation or expansion of the liner but the fixation of the liner to the esophageal wall is achieved by means of mechanical attachment e.g. spikes, hooks or by glue or the like.

The Liner:

In one embodiment, the liner is a tubular structure with two ends, proximal and distal, and a side opening mechanism between the two ends. In a preferred embodiment, the liner is transparent for better vision/placement; in another embodiment the liner is made of biodegradable material e.g. starch or other food or biodegradable materials that will be digested in a day or two, or other acceptable time frame. The liner may be made of expansile or non expansile material as above. In a preferred embodiment, the proximal and distal openings are covered with a slotted diaphragm that allows the carrying scope or any other surgical instrument to pass through, but will seal the ends when no device is passed in either end. The side opening mechanism can be a simple slot, an iris, a flap, a shutter, double shutters or opposing ends, or any simple structures that allow for opening, closure or partial closure of the side opening.

The Obturator:

After the liner is situated in place at the target segment, with the side opening mechanism facing the lesion posteriorly towards the vertebral column, an opening device or obturator is passed from the mouth to the proximal end of the liner across the slotted diaphragm and through the side opening mechanism to start a perforation in the esophageal wall. In a preferred embodiment of the invention, the obturator is a blunt dissection tool with a sharp short needle at the tip that is retracted after initial partial penetration into the mucosa. The blunt head is pushed out of the esophageal wall and a surgical perforation is made opposite and external to the side opening mechanism. The obturator is removed from the field.

The Therapeutic Scope:

a specialized surgical scope is passed from the mouth to the esophageal lumen across the proximal end of the liner into the side opening mechanism (in its fully open phase). The scope is passed through the esophageal wall penetration to the surgical field of the cervical vertebral column. Surgical interventions are applied according to the specific pathology. In a preferred embodiment of the invention, lysis and absorption of the nucleus bulbosus of the intervertebral disk is followed by fixation of the vertebral bodies. It is understood that any form of spinal or vertebral procedure can be achieved from this location. The operating scope can be of any known type, including flexible, semi rigid, robotic, manual or remotely (telemedically) operated.

After the procedure is completed, the side opening mechanism is closed, covering the esophageal wall mucosal incision until it heals spontaneously by first intention. This usually takes place within hours to a day. After that the liner can either be removed or left to be digested spontaneously. The upper and lower end of the liner are sealed as mentioned above which prevents secretions from above (saliva) or below (gastric content) from spoiling the surgical field or track into the liner lumen.

Other Features

The current invention provides specific devices and methods to facilitate the performance of all surgical, orthopedic and neurosurgical diagnostic and therapeutic procedures in the neck and thoracic region. Such procedures are currently done by conventional surgical approaches. Conventional approaches are not satisfactory and highly invasive. In the case of Cervical Spine surgery for example, said procedures either include the anterior or the posterior neck approaches. The anterior approach involves extensive dissection through multiple layers and structures of the neck with resultant intra operative and post operative morbidity and complications and delayed painful recovery plus the external skin wounds. The posterior approach is less extensive in terms of surgical dissections but is more risky because it involves manipulation of the cervical spinal cord, in cases of cervical discectomy for example. The invention teaches the Transesophageal approach to the neck. The transesophageal cervical approach to the vertebral column and cervical spinal cord provides a short, fast and accurate access in a minimally invasive fashion that obviates the disadvantages of either the anterior or posterior approaches. It can be done without the need of general anesthesia. Many other medical, orthopedic and neurosurgical procedures can be also performed using the transesophageal approach, including, in particular and without limitation, known procedures for surgery in the cervical and thoracic cavities.

In another aspect, a liner may further comprise other types of component. In one embodiment, a liner carries at least one means for sensing conditions, reporting data, and/or applying a local stimulus. This can allow monitoring of local conditions without additional connections to carry data, or to exert local effects (such as cautery), or simply to allow accurate detection of position via RFID and the like. Also included are simple locating means such as radio-opaque materials, or luminescent materials to allow local optical detection.

Having fully described the invention, it will be seen that the objects set forth above are efficiently attained. Since certain changes may be made in the above method and constructions while obtaining the same effect, it is intended that all matter contained in the above description or shown in the accompanying drawings shall be interpreted as illustrative and not in a limiting sense. It is also to be understood that the following claims are intended to cover all of the generic features of the invention described herein.

The invention claimed is:

1. A method of performing transesophageal surgery, wherein the method comprises:
   inserting a liner, having a first proximate end, a second distal end and a body portion connecting the first proximate end and the second distal end, through a mouth of a patient;
   positioning the first proximate end such that the first proximate end is closer to the mouth of the patient and open to a body lumen, positioning the second distal end so that the second distal end is more distal from the mouth and so that the liner is proximate to tissue of the body lumen, wherein the act of positioning the liner further includes applying at least a portion of a longitudinal wall of the body portion of the liner to the tissue of the body lumen;
   inserting a distal portion of a surgical instrument through the mouth of the patient and passing the distal portion of the surgical instrument by the first proximate end of the liner and adjacent to the longitudinal wall of the body portion of the liner; and
   extending the distal portion of the surgical instrument through the longitudinal wall of the body portion of the liner and entirely through the tissue of the body lumen, wherein the liner is placed in the patient's esophagus, and the surgical instrument is passed entirely through the liner and the esophagus.

2. The method of claim 1, wherein the liner is a barrier and comprises a complete or partial opening to allow devices to go through an esophageal wall to a target outside the esophageal wall after the liner and the esophageal wall have been penetrated to create an opening.

3. The method of claim 2 wherein the longitudinal wall includes a side opening, and the method further comprises closing the side opening spontaneously upon withdrawal of an instrument.

4. The method of claim 1 wherein the method further comprises performing any one or more of: tumor excision, tumor biopsy, placement of drugs, placement of tissues, placement of radioactive materials, bronchial biopsy, airway bypass, manipulation of great vessels of the thorax, and pulmonary artery bypass.

5. The method of claim 1 wherein the method further comprises performing a surgical procedure, wherein the procedure to be performed is one or more of disk surgery, vertebral column surgery, spinal cord surgery, nerve root surgery, spinal and paraspinal muscle surgery, vascular surgery, oncologic surgery, laser surgery, delivery of energy to tissue, delivery of tissue or genetic material, delivery of surgical devices, delivery of cardiac pacemaker or diaphragmatic pace maker, and performance of procedures affecting the esophagus itself including fundoplication, and stomach pacemaker implantation.

6. The method of claim 1 wherein the method further comprises performing a surgical procedure, wherein the procedure to be performed is one or more cardiac procedures including mapping, cardiac ablation, valve surgery, closure of septal defects, laser surgery, delivery of energy to the heart and related structures for pacing or to enhance contractility, delivery of drugs or genetic material, and delivery of surgical devices to the heart and related structures.

7. The method of claim 1 wherein the method further comprises performing a surgical procedure, wherein the procedure to be performed is one or more of procedures on the lungs, bronchi, nerves, lymphatics, great vessels of the thorax, bony or cartilaginous structures, diaphragm, phrenic nerve, gastroesophageal junction and on the esophagus itself, including the delivery of an esophageal band for satiety or an intra-esophageal valve for reflux.

8. A method for performing surgery in which at least one liner is placed in a tubular body lumen, including any one or more of the esophagus, the intestine, the genitourinary (GU) tract, the cardiovascular system, the pulmonary system, the canaliculi of the inner ear, and the lymphatic system, the method comprising:
   inserting at least one liner having a first proximate end, a second distal end and a body portion connecting the first proximate end and the second distal end, and having at least one side opening, through a respective body opening of a patient;
   positioning the first proximate end of the at least one liner such that the first proximate end is closer to an open end of the body lumen,
   positioning the second distal end of the least one liner so that the second distal end is more distal from the open end of the body lumen and so that the liner is proximate to tissue of the body lumen, inserting a distal portion of a surgical instrument through the respective body lumen of the patient and passing the distal portion of the surgical instrument by the first proximate end of at least one liner and adjacent to a longitudinal wall of the body portion of the at least one liner;

extending the distal portion of the surgical instrument through the longitudinal wall of the body portion of the at least one liner and entirely through the tissue of the body lumen;

generating more than one opening entirely through the body lumen through either at least one liner having more than one side opening or more than one liner having at least one opening; and performing a surgical procedure on a body member that is separate and away from the body lumen.

9. A method as in claim 8 where said opening is sprayed or painted with sealant material to enhance closure of the perforation site.

10. A method as in claim 8 wherein the surgical instrument includes at least one of an operating scope that is a conventional scope, a therapeutic scope with custom made specifications, a robotic scope, and a remotely operated scope.

* * * * *